(12) United States Patent
Kirn

(10) Patent No.: US 10,970,261 B2
(45) Date of Patent: Apr. 6, 2021

(54) SYSTEM AND METHOD FOR DATA QUALITY MONITORS

(71) Applicant: Palantir Technologies, Inc., Palo Alto, CA (US)

(72) Inventor: Malina Kirn, Arlington, VA (US)

(73) Assignee: Palantir Technologies Inc., Denver, CO (US)

( * ) Notice: Subject to any disclaimer, the term of this patent is extended or adjusted under 35 U.S.C. 154(b) by 606 days.

(21) Appl. No.: 15/158,410

(22) Filed: May 18, 2016

(65) Prior Publication Data

US 2016/0342629 A1  Nov. 24, 2016

Related U.S. Application Data

(63) Continuation of application No. 14/094,418, filed on Dec. 2, 2013, now Pat. No. 9,348,851, which is a (Continued)

(51) Int. Cl.
| | |
|---|---|
| *G06F 11/00* | (2006.01) |
| *G06F 16/215* | (2019.01) |
| *G06F 16/23* | (2019.01) |
| *G06F 16/2455* | (2019.01) |
| *G06F 11/07* | (2006.01) |

(Continued)

(52) U.S. Cl.
CPC ........ *G06F 16/215* (2019.01); *A61B 17/0057* (2013.01); *A61B 17/0401* (2013.01); *G06F 3/0482* (2013.01); *G06F 3/04847* (2013.01); *G06F 11/0751* (2013.01); *G06F 16/2365* (2019.01); *G06F 16/24556* (2019.01); *A61B 2017/00004* (2013.01); *A61B 2017/00623* (2013.01); *A61B 2017/00659* (2013.01);

(Continued)

(58) Field of Classification Search
CPC combination set(s) only.
See application file for complete search history.

(56) References Cited

U.S. PATENT DOCUMENTS

| | | | |
|---|---|---|---|
| 5,826,021 | A | 10/1998 | Mastors et al. |
| 5,832,218 | A | 11/1998 | Gibbs et al. |

(Continued)

FOREIGN PATENT DOCUMENTS

| | | |
|---|---|---|
| AU | 2014203669 | 5/2016 |
| CN | 102054015 | 5/2014 |

(Continued)

OTHER PUBLICATIONS

Bhattacharya et al., "Collective Entity Resolution in Relational Data," ACM Transactions on Knowledge Discovery from Data (TKDD, Association for Computing Machinery, Inc., vol. 1, No. 1, Mar. 1, 2007, pp. 5-es.

(Continued)

*Primary Examiner* — Loan L. T. Truong
(74) *Attorney, Agent, or Firm* — Knobbe, Martens, Olson & Bear LLP

(57) ABSTRACT

Systems and methods are presented for data quality monitoring. Data quality monitors may be created and configured to identify objects with specified data quality issues and/or property values. Objects identified by a data quality monitor can be presented to users for confirmation and resolution. Properties used by the data quality monitor to match objects may also be displayed to users.

14 Claims, 14 Drawing Sheets

Related U.S. Application Data continuation of application No. 13/935,861, filed on Jul. 5, 2013, now Pat. No. 8,601,326.

(51) Int. Cl.
*A61B 17/00* (2006.01)
*A61B 17/04* (2006.01)
*G06F 3/0482* (2013.01)
*G06F 3/0484* (2013.01)

(52) U.S. Cl.
CPC ............... *A61B 2017/0409* (2013.01); *A61B 2017/0456* (2013.01); *A61B 2017/0459* (2013.01)

(56) References Cited

U.S. PATENT DOCUMENTS

| | | | |
|---|---|---|---|
| 5,878,434 A | 3/1999 | Draper et al. | |
| 5,897,636 A | 4/1999 | Kaeser | |
| 5,966,706 A | 10/1999 | Biliris et al. | |
| 5,978,475 A | 11/1999 | Schneier et al. | |
| 6,006,242 A | 12/1999 | Poole et al. | |
| 6,057,757 A | 5/2000 | Arrowsmith et al. | |
| 6,101,479 A | 8/2000 | Shaw | |
| 6,134,582 A | 10/2000 | Kennedy | |
| 6,243,717 B1 | 6/2001 | Gordon et al. | |
| 6,347,374 B1* | 2/2002 | Drake | G06F 21/554 709/224 |
| 6,430,305 B1 | 8/2002 | Decker | |
| 6,463,404 B1 | 10/2002 | Appleby | |
| 6,519,627 B1 | 2/2003 | Dan et al. | |
| 6,523,019 B1 | 2/2003 | Borthwick | |
| 6,725,240 B1 | 4/2004 | Asad et al. | |
| 7,017,046 B2 | 3/2006 | Doyle et al. | |
| 7,058,648 B1 | 6/2006 | Lightfoot et al. | |
| 7,089,541 B2 | 8/2006 | Ungar | |
| 7,117,430 B2 | 10/2006 | Maguire et al. | |
| 7,403,942 B1 | 7/2008 | Bayliss | |
| 7,461,158 B2 | 12/2008 | Rider et al. | |
| 7,627,489 B2 | 12/2009 | Schaeffer et al. | |
| 7,739,246 B2* | 6/2010 | Mooney | G06F 17/30578 707/687 |
| 7,757,220 B2 | 7/2010 | Griffith et al. | |
| 7,770,032 B2 | 8/2010 | Nesta et al. | |
| 7,801,871 B2 | 9/2010 | Gosnell | |
| 7,877,421 B2 | 1/2011 | Berger et al. | |
| 7,912,842 B1* | 3/2011 | Bayliss | G06F 17/30545 707/749 |
| 7,962,495 B2* | 6/2011 | Jain | G06F 17/2705 706/2 |
| 8,117,022 B2 | 2/2012 | Linker | |
| 8,126,848 B2 | 2/2012 | Wagner | |
| 8,190,893 B2 | 5/2012 | Benson et al. | |
| 8,290,838 B1 | 10/2012 | Thakur et al. | |
| 8,302,855 B2 | 11/2012 | Ma et al. | |
| 8,364,642 B1 | 1/2013 | Garrod | |
| 8,386,377 B1 | 2/2013 | Xiong et al. | |
| 8,392,556 B2 | 3/2013 | Goulet et al. | |
| 8,417,715 B1 | 4/2013 | Bruckhaus et al. | |
| 8,429,527 B1 | 4/2013 | Arbogast | |
| 8,527,475 B1* | 9/2013 | Rammohan | G06F 17/30489 707/692 |
| 8,554,719 B2 | 10/2013 | McGrew | |
| 8,601,326 B1 | 12/2013 | Kirn | |
| 8,639,552 B1 | 1/2014 | Chen et al. | |
| 8,688,573 B1 | 4/2014 | Ruknoic et al. | |
| 8,700,569 B1* | 4/2014 | Wilson | G06F 17/303 707/626 |
| 8,798,354 B1 | 8/2014 | Bunzel et al. | |
| 8,812,444 B2 | 8/2014 | Garrod et al. | |
| 8,838,538 B1 | 9/2014 | Landau et al. | |
| 8,855,999 B1 | 10/2014 | Elliot | |
| 8,903,717 B2 | 12/2014 | Elliot | |
| 8,924,388 B2 | 12/2014 | Elliot et al. | |
| 8,924,389 B2 | 12/2014 | Elliot et al. | |
| 8,938,434 B2 | 1/2015 | Jain et al. | |
| 8,938,686 B1 | 1/2015 | Erenrich et al. | |
| 9,105,000 B1 | 8/2015 | White et al. | |
| 9,129,046 B2* | 9/2015 | Bess | G06F 16/22 |
| 9,129,219 B1* | 9/2015 | Robertson | G06Q 10/10 |
| 9,230,060 B2 | 1/2016 | Friedlander et al. | |
| 9,286,373 B2 | 3/2016 | Elliot et al. | |
| 9,348,499 B2 | 5/2016 | Aymeloglu et al. | |
| 9,348,851 B2* | 5/2016 | Kim | A61B 17/0401 |
| 9,483,546 B2* | 11/2016 | Erenrich | G06F 16/2465 |
| 10,127,289 B2* | 11/2018 | Manning | G06F 16/35 |
| 10,140,664 B2* | 11/2018 | Erenrich | G06Q 40/10 |
| 10,198,515 B1* | 2/2019 | White | G06Q 10/06398 |
| 10,452,678 B2* | 10/2019 | Kumar | G06F 16/904 |
| 2002/0035590 A1 | 3/2002 | Eibach et al. | |
| 2002/0095360 A1 | 7/2002 | Joao | |
| 2002/0103705 A1 | 8/2002 | Brady | |
| 2002/0112157 A1 | 8/2002 | Doyle et al. | |
| 2002/0194058 A1 | 12/2002 | Eldering | |
| 2003/0061132 A1 | 3/2003 | Mason et al. | |
| 2003/0074187 A1 | 4/2003 | Ait-Mokhtar et al. | |
| 2003/0088438 A1 | 5/2003 | Maughan et al. | |
| 2003/0093401 A1 | 5/2003 | Czahkowski et al. | |
| 2003/0105759 A1 | 6/2003 | Bess et al. | |
| 2003/0115481 A1 | 6/2003 | Baird et al. | |
| 2003/0126102 A1 | 7/2003 | Borthwick | |
| 2003/0171942 A1 | 9/2003 | Gaito | |
| 2003/0177112 A1 | 9/2003 | Gardner | |
| 2003/0182313 A1 | 9/2003 | Federwisch et al. | |
| 2003/0212718 A1 | 11/2003 | Tester | |
| 2004/0003009 A1 | 1/2004 | Wilmot | |
| 2004/0006523 A1 | 1/2004 | Coker | |
| 2004/0034570 A1 | 2/2004 | Davis | |
| 2004/0083466 A1 | 4/2004 | Dapp et al. | |
| 2004/0088177 A1 | 5/2004 | Travis et al. | |
| 2004/0117387 A1 | 6/2004 | Civetta et al. | |
| 2004/0153451 A1 | 8/2004 | Phillips et al. | |
| 2004/0210763 A1 | 10/2004 | Jonas | |
| 2004/0236688 A1 | 11/2004 | Bozeman | |
| 2005/0010472 A1 | 1/2005 | Quatse et al. | |
| 2005/0097441 A1 | 5/2005 | Herbach et al. | |
| 2005/0102328 A1 | 5/2005 | Ring et al. | |
| 2005/0131935 A1 | 6/2005 | O'Leary et al. | |
| 2005/0182780 A1* | 8/2005 | Forman | G06F 17/30303 |
| 2005/0262493 A1 | 11/2005 | Schmidt et al. | |
| 2005/0262512 A1 | 11/2005 | Schmidt et al. | |
| 2006/0010130 A1 | 1/2006 | Leff et al. | |
| 2006/0080283 A1 | 4/2006 | Shipman | |
| 2006/0080316 A1 | 4/2006 | Gilmore et al. | |
| 2006/0085483 A1* | 4/2006 | Mooney | G06F 16/273 |
| 2006/0143075 A1 | 6/2006 | Carr et al. | |
| 2006/0161558 A1 | 7/2006 | Tamma et al. | |
| 2006/0178954 A1 | 8/2006 | Thukral et al. | |
| 2006/0209085 A1 | 9/2006 | Wong et al. | |
| 2006/0218206 A1 | 9/2006 | Bourbonnais et al. | |
| 2006/0218491 A1 | 9/2006 | Grossman et al. | |
| 2006/0253502 A1 | 11/2006 | Raman et al. | |
| 2007/0000999 A1 | 1/2007 | Kubo et al. | |
| 2007/0039018 A1* | 2/2007 | Saslow | G06Q 30/02 725/22 |
| 2007/0067285 A1 | 3/2007 | Blume | |
| 2007/0162454 A1 | 7/2007 | D'Albora et al. | |
| 2007/0178501 A1 | 8/2007 | Rabinowitz et al. | |
| 2007/0192122 A1 | 8/2007 | Routson et al. | |
| 2007/0233756 A1 | 10/2007 | D'Souza et al. | |
| 2007/0271317 A1 | 11/2007 | Carmel | |
| 2007/0284433 A1 | 12/2007 | Domenica et al. | |
| 2007/0295797 A1 | 12/2007 | Herman et al. | |
| 2007/0299697 A1 | 12/2007 | Friedlander et al. | |
| 2008/0005063 A1 | 1/2008 | Seeds | |
| 2008/0104407 A1 | 5/2008 | Horne et al. | |
| 2008/0126344 A1 | 5/2008 | Hoffman et al. | |
| 2008/0126951 A1 | 5/2008 | Sood et al. | |
| 2008/0140387 A1 | 6/2008 | Linker | |
| 2008/0168054 A1 | 7/2008 | Lee et al. | |
| 2008/0168531 A1* | 7/2008 | Gavin | H04L 63/1408 726/1 |
| 2008/0195672 A1 | 8/2008 | Hamel et al. | |

(56) References Cited

U.S. PATENT DOCUMENTS

| | | |
|---|---|---|
| 2008/0201580 A1 | 8/2008 | Savitzky et al. |
| 2008/0208735 A1 | 8/2008 | Balet et al. |
| 2008/0228467 A1 | 9/2008 | Womack et al. |
| 2008/0267386 A1 | 10/2008 | Cooper |
| 2008/0270316 A1 | 10/2008 | Guidotti et al. |
| 2008/0281580 A1 | 11/2008 | Zabokritski |
| 2008/0301042 A1 | 12/2008 | Patzer |
| 2008/0313132 A1 | 12/2008 | Hao et al. |
| 2009/0012973 A1* | 1/2009 | Moon ............... G06F 21/10 |
| 2009/0055487 A1 | 2/2009 | Moraes et al. |
| 2009/0094270 A1 | 4/2009 | Alirez et al. |
| 2009/0106178 A1 | 4/2009 | Chu |
| 2009/0106242 A1 | 4/2009 | McGrew |
| 2009/0112745 A1 | 4/2009 | Stefanescu |
| 2009/0157732 A1 | 6/2009 | Hao et al. |
| 2009/0164387 A1 | 6/2009 | Armstrong et al. |
| 2009/0187546 A1 | 7/2009 | Whyte et al. |
| 2009/0216562 A1 | 8/2009 | Faulkner et al. |
| 2009/0228365 A1 | 9/2009 | Tomchek et al. |
| 2009/0228507 A1* | 9/2009 | Jain ............... G06F 40/205 |
| 2009/0228701 A1 | 9/2009 | Lin |
| 2009/0249244 A1 | 10/2009 | Robinson et al. |
| 2009/0271343 A1 | 10/2009 | Vaiciulis et al. |
| 2009/0299830 A1 | 12/2009 | West et al. |
| 2009/0307049 A1 | 12/2009 | Elliott et al. |
| 2009/0313311 A1 | 12/2009 | Hoffmann et al. |
| 2009/0313463 A1 | 12/2009 | Pang et al. |
| 2009/0319515 A1 | 12/2009 | Minton et al. |
| 2010/0057622 A1 | 3/2010 | Faith et al. |
| 2010/0070531 A1 | 3/2010 | Aymeloglu et al. |
| 2010/0070842 A1 | 3/2010 | Aymeloglu et al. |
| 2010/0076813 A1 | 3/2010 | Ghosh et al. |
| 2010/0082541 A1 | 4/2010 | Kottomtharayil |
| 2010/0082671 A1 | 4/2010 | Li et al. |
| 2010/0098318 A1 | 4/2010 | Anderson |
| 2010/0114817 A1 | 5/2010 | Broeder et al. |
| 2010/0114831 A1 | 5/2010 | Gilbert et al. |
| 2010/0115353 A1* | 5/2010 | Ottley ............ G01R 31/31855 714/726 |
| 2010/0125470 A1 | 5/2010 | Chisholm |
| 2010/0145909 A1 | 6/2010 | Ngo |
| 2010/0204983 A1 | 8/2010 | Chung et al. |
| 2010/0211550 A1 | 8/2010 | Daniello et al. |
| 2010/0306285 A1 | 12/2010 | Shah et al. |
| 2010/0332008 A1* | 12/2010 | Knipfer ............ G05B 19/042 700/103 |
| 2011/0004626 A1* | 1/2011 | Naeymi-Rad ......... G06N 7/005 707/776 |
| 2011/0004702 A1* | 1/2011 | Tsofi ............... H04L 67/1095 709/248 |
| 2011/0010401 A1* | 1/2011 | Adams ............ G06F 16/221 707/805 |
| 2011/0060910 A1 | 3/2011 | Gormish et al. |
| 2011/0066497 A1 | 3/2011 | Gopinath et al. |
| 2011/0093327 A1 | 4/2011 | Fordyce, III et al. |
| 2011/0099133 A1 | 4/2011 | Chang et al. |
| 2011/0131547 A1 | 6/2011 | Elaasar |
| 2011/0173093 A1 | 7/2011 | Psota et al. |
| 2011/0208565 A1 | 8/2011 | Ross et al. |
| 2011/0208822 A1 | 8/2011 | Rathod |
| 2011/0225586 A1 | 9/2011 | Bentley et al. |
| 2011/0238408 A1 | 9/2011 | Larcheveque et al. |
| 2011/0252282 A1 | 10/2011 | Meek et al. |
| 2011/0258216 A1 | 10/2011 | Supakkul et al. |
| 2012/0013684 A1 | 1/2012 | Robertson et al. |
| 2012/0022945 A1 | 1/2012 | Falkenborg et al. |
| 2012/0059853 A1 | 3/2012 | Jagota |
| 2012/0065987 A1 | 3/2012 | Farooq et al. |
| 2012/0078595 A1 | 3/2012 | Balandin et al. |
| 2012/0084287 A1 | 4/2012 | Lakshminarayan et al. |
| 2012/0089606 A1 | 4/2012 | Eshwar et al. |
| 2012/0136804 A1 | 5/2012 | Lucia |
| 2012/0150860 A1 | 6/2012 | Bhamidipati et al. |
| 2012/0191446 A1 | 7/2012 | Binsztok et al. |
| 2012/0215784 A1 | 8/2012 | King et al. |
| 2012/0290879 A1 | 11/2012 | Shibuya et al. |
| 2013/0006947 A1* | 1/2013 | Akinyemi ............ G06F 16/178 707/687 |
| 2013/0016106 A1 | 1/2013 | Yip et al. |
| 2013/0091084 A1 | 4/2013 | Lee |
| 2013/0096968 A1 | 4/2013 | Van Pelt et al. |
| 2013/0097130 A1* | 4/2013 | Bingol ............... G06F 16/273 707/694 |
| 2013/0124193 A1 | 5/2013 | Holmberg |
| 2013/0132348 A1 | 5/2013 | Garrod |
| 2013/0151453 A1 | 6/2013 | Bhanot et al. |
| 2013/0166480 A1 | 6/2013 | Popescu et al. |
| 2013/0198565 A1 | 8/2013 | Mancoridis et al. |
| 2013/0226879 A1* | 8/2013 | Talukder ............ G06F 16/20 707/690 |
| 2013/0226944 A1 | 8/2013 | Baid et al. |
| 2013/0246316 A1 | 9/2013 | Zhao et al. |
| 2013/0263019 A1 | 10/2013 | Castellanos et al. |
| 2013/0325826 A1 | 12/2013 | Agarwal et al. |
| 2014/0006404 A1 | 1/2014 | McGrew et al. |
| 2014/0032556 A1 | 1/2014 | Bayliss |
| 2014/0089339 A1 | 3/2014 | Siddiqui et al. |
| 2014/0095363 A1* | 4/2014 | Caldwell ............ G06Q 20/10 705/35 |
| 2014/0108074 A1 | 4/2014 | Miller et al. |
| 2014/0164379 A1* | 6/2014 | Jojgov ............ G06F 17/30598 707/737 |
| 2014/0222793 A1* | 8/2014 | Sadkin ............ G06F 16/24578 707/723 |
| 2014/0279299 A1 | 9/2014 | Erenrich |
| 2014/0297640 A1 | 10/2014 | Duftler et al. |
| 2014/0358829 A1 | 12/2014 | Hurwitz |
| 2015/0012509 A1 | 1/2015 | Kirn |
| 2015/0019991 A1* | 1/2015 | Kristjánsson ....... H04L 41/0853 715/747 |
| 2015/0046481 A1 | 2/2015 | Elliot |
| 2015/0100907 A1 | 4/2015 | Erenrich et al. |
| 2015/0106379 A1 | 4/2015 | Elliot et al. |
| 2015/0188715 A1 | 7/2015 | Castelluci et al. |
| 2015/0227542 A1* | 8/2015 | Thatavarthy .......... G06F 16/248 707/692 |
| 2016/0070706 A1* | 3/2016 | Lee ............... G06F 17/30864 707/751 |
| 2016/0171075 A1* | 6/2016 | Erenrich ............ G06F 16/2462 707/738 |
| 2017/0052958 A1 | 2/2017 | Manning et al. |
| 2018/0285595 A1* | 10/2018 | Jessen ............... G06F 21/6245 |

FOREIGN PATENT DOCUMENTS

| | | |
|---|---|---|
| DE | 102014204827 | 9/2014 |
| DE | 102014204830 | 9/2014 |
| DE | 102014204834 | 9/2014 |
| DE | 102014213036 | 1/2015 |
| EP | 1566758 | 8/2005 |
| EP | 1962222 | 8/2008 |
| EP | 2487610 | 8/2012 |
| EP | 2551799 | 1/2013 |
| EP | 2778913 | 9/2014 |
| EP | 2778914 | 9/2014 |
| EP | 2897051 | 7/2015 |
| EP | 3035214 | 6/2016 |
| EP | 3133511 | 1/2017 |
| GB | 2366498 | 3/2002 |
| GB | 2513472 | 10/2014 |
| GB | 2513721 | 11/2014 |
| GB | 2517582 | 2/2015 |
| NL | 2013134 | 1/2015 |
| WO | WO 2005/010685 | 2/2005 |
| WO | WO 2009/051987 | 4/2009 |
| WO | WO 2010/030919 | 3/2010 |
| WO | WO 2011/017289 | 5/2011 |
| WO | WO 2011/071833 | 6/2011 |
| WO | WO 2012/061162 | 5/2012 |

(56) References Cited

FOREIGN PATENT DOCUMENTS

| WO | WO 2012/079836 | 6/2012 |
|----|----------------|--------|
| WO | WO 2013/067077 | 5/2013 |

OTHER PUBLICATIONS

Brandel, Mary, "Data Loss Prevention Dos and Don'ts," <http://web.archive.org/web/20080724024847/http://www.csoonline.com/article/221272/Dos_and_Don_ts_for_Data_Loss_Prevention>, Oct. 10, 2007, pp. 5.
Draisbach et al., "A Comparison and Generalization of Blocking and Windowing Algorithm for Duplicate Detection," Aug. 24, 2009, retrieved from https://hpi.de/fileadmin/user_upload/fachgebiete/naumann/publication/2009/QDB09_crc.pdf.
Elmagarmid et al., "Duplicate Record Detection: A Survey," IEEE Transactions on Knowledge and Data Engineering, IEEE Service Center, Los Alamitos, California, US, vol. 19, No. 1, Jan. 1, 2007, pp. 1-16.
Getoor et al., "Entity Resolution for Big Data," Aug. 11, 2013, retrieved from http://www.umiacs.umd.edu/~geotoor/Tutorials/ER_KDD2013.pdf.
Kardes et al., "Graph-based Approaches for Organization Entity Resolution in MapReduce," Proceedings of the TextGraphs-8 Workshop, Oct. 18, 2013, pp. 70-78.
Kopcke et al., "Frameworks for Entity Matching: A Comparison," Data & Knowledge Engineering, vol. 69, No. 2, Feb. 1, 2010, pp. 197-210.
Pythagoras Communications Ltd., "Microsoft CRM Duplicate Detection," Sep. 13, 2011, https://www.youtube.com/watch?v=j-7Qs0D0Kc.
Wikipedia, "Record Linkage," May 9, 2015, retrieved from https://web.archive.org/web/20150509130215/http://en.wikipedia.org/wiki/Record_Linkage.
Notice of Allowance for U.S. Appl. No. 12/556,307 dated Jan. 4, 2016.
Notice of Allowance for U.S. Appl. No. 14/094,418 dated Jan. 25, 2016.
Official Communication for European Patent Application No. 16184820.5 dated Jan. 3, 2017.
Official Communication for Great Britain Patent Application No. 1411984.6 dated Aug. 1, 2016.
Official Communication for U.S. Appl. No. 15/233,149 dated Apr. 21, 2017.
Official Communication for U.S. Appl. No. 15/233,149 dated Aug. 25, 2017.
"A Tour of Pinboard," <http://pinboard.in/tour> as printed May 15, 2014 in 6 pages.
Anonymous, "A Real-World Problem of Matching Records," Nov. 2006, <http://grupoweb.upf.es/bd-web/slides/ullman.pdf> pp. 1-16.
Chaudhuri et al., "An Overview of Business Intelligence Technology," Communications of the ACM, Aug. 2011, vol. 54, No. 8.
Delicious, <http://delicious.com/> as printed May 15, 2014 in 1 page.
"E-MailRelay," <http://web.archive.org/web/20080821175021/http://emailrelay.sourceforge.net/> Aug. 21, 2008, pp. 2.
Geiger, Jonathan G., "Data Quality Management, The Most Critical Initiative You Can Implement", Data Warehousing, Management and Quality, Paper 098-29, SUGI 29, Intelligent Solutions, Inc., Bounder, CO, pp. 14, accessed Oct. 3, 2013.
Gu et al., "Record Linkage: Current Practice and Future Directions," Jan. 15, 2004, pp. 32.
Hua et al., "A Multi-attribute Data Structure with Parallel Bloom Filters for Network Services", HiPC 2006, LNCS 4297, pp. 277-288, 2006.
Johnson, Maggie "Introduction to YACC and Bison", Handout 13, Jul. 8, 2005, in 11 pages, Apr. 2, 2018.
Johnson, Steve, "Access 2013 on demand," Access 2013 on Demand, May 9, 2013, Que Publishing.
Lim et al., "Resolving Attribute Incompatibility in Database Integration: An Evidential Reasoning Approach," Department of Computer Science, University of Minnesota, 1994, <http://reference.kfupm.edu.sa/content/r/e/resolving_attribute_incompatibility_in_d_531691.pdf> pp. 1-10.
Litwin et al., "Multidatabase Interoperability," IEEE Computer, Dec. 1986, vol. 19, No. 12, http://www.lamsade.dauphine.fr/~litwin/mdb-interoperability.pdf, pp. 10-18.
Ma et al., "A New Approach to Secure Logging," ACM Transactions on Storage, vol. 5, No. 1, Article 2, Published Mar. 2009, 21 pages.
Nadeau et al., "A Survey of Named Entity Recognition and Classification," Jan. 15, 2004, pp. 20.
Nin et al., "On the Use of Semantic Blocking Techniques for Data Cleansing and Integration," 11th International Database Engineering and Applications Symposium, 2007, pp. 9.
Qiang et al., "A Mutual-Information-Based Approach to Entity Reconciliation in Heterogeneous Databases," Proceedings of 2008 International Conference on Computer Science & Software Engineering, IEEE Computer Society, New York, NY, Dec. 12-14, 2008, pp. 666-669.
Schneier et al., "Automatic Event Stream Notarization Using Digital Signatures," Security Protocols, International Workshop Apr. 1996 Proceedings, Springer-Veriag, 1997, pp. 155-169, https://schneier.com/paper-event-stream.pdf.
Schneier et al., "Cryptographic Support for Secure Logs on Untrusted Machines," The Seventh USENIX Security Symposium Proceedings, USENIX Press, Jan. 1998, pp. 53-62, https://www.schneier.com/paper-secure-logs.pdf.
Sekine et al., "Definition, Dictionaries and Tagger for Extended Named Entity Hierarchy," May 2004, pp. 1977-1980.
Wang et al., "Research on a Clustering Data De-Duplication Mechanism Based on Bloom Filter," IEEE 2010, 5 pages.
Waters et al., "Building an Encrypted and Searchable Audit Log," Published Jan. 9, 2004, 11 pages, http://www.parc.com/content/attachments/building_encrypted_searchable_5059_parc.pdf.
Wikipedia, "Multimap," Jan. 1, 2013, https://en.wikipedia.org/w/index.php?title=Multimap&oldid=530800748.
Zhao et al., "Entity Matching Across Heterogeneous Data Sources: An Approach Based on Constrained Cascade Generalization," Data & Knowledge Engineering, vol. 66, No. 3, Sep. 2008, pp. 368-381.
Notice of Allowance for U.S. Appl. No. 14/223,918 dated Jan. 6, 2016.
Notice of Allowance for U.S. Appl. No. 14/304,741 dated Apr. 7, 2015.
Notice of Allowance for U.S. Appl. No. 14/552,336 dated Nov. 3, 2015.
Official Communication for Australian Patent Application No. 2014201506 dated Feb. 27, 2015.
Official Communication for Australian Patent Application No. 2014201507 dated Feb. 27, 2015.
Official Communication for Australian Patent Application No. 2014203669 dated May 29, 2015.
Official Communication for European Patent Application No. 09813700.3 dated Apr. 3, 2014.
Official Communication for European Patent Application No. 14158958.0 dated Apr. 16, 2015.
Official Communication for European Patent Application No. 14158958.0 dated Jun. 3, 2014.
Official Communication for European Patent Application No. 14158977.0 dated Jun. 10, 2014.
Official Communication for European Patent Application No. 14158977.0 dated Apr. 16, 2015.
Official Communication for European Patent Application No. 14199180.2 dated Jun. 22, 2015.
Official Communication for European Patent Application No. 14199180.2 dated Aug. 31, 2015.
Official Communication for Great Britain Patent Application No. 1404486.1 dated May 21, 2015.
Official Communication for Great Britain Patent Application No. 1404486.1 dated Aug. 27, 2014.
Official Communication for Great Britain Patent Application No. 1404489.5 dated May 21, 2015.

(56) References Cited

OTHER PUBLICATIONS

Official Communication for Great Britain Patent Application No. 1404489.5 dated Aug. 27, 2014.
Official Communication for Great Britain Patent Application No. 1404499.4 dated Jun. 11, 2015.
Official Communication for Great Britain Patent Application No. 1404499.4 dated Aug. 20, 2014.
Official Communication for Great Britain Patent Application No. 1411984.6 dated Dec. 22, 2014.
Official Communication for Netherlands Patent Application No. 2012417 dated Sep. 18, 2015.
Official Communication for Netherlands Patent Application No. 2012421 dated Sep. 18, 2015.
Official Communication for Netherlands Patent Application No. 2012438 dated Sep. 21, 2015.
Official Communication for Netherlands Patent Application No. 2013134 dated Apr. 20, 2015.
Official Communication for New Zealand Patent Application No. 622389 dated Mar. 20, 2014.
Official Communication for New Zealand Patent Application No. 622404 dated Mar. 20, 2014.
Official Communication for New Zealand Patent Application No. 622439 dated Mar. 24, 2014.
Official Communication for New Zealand Patent Application No. 622439 dated Jun. 6, 2014.
Official Communication for New Zealand Patent Application No. 622473 dated Jun. 19, 2014.
Official Communication for New Zealand Patent Application No. 622473 dated Mar. 27, 2014.
Official Communication for New Zealand Patent Application No. 627061 dated Jul. 14, 2014.
Official Communication for New Zealand Patent Application No. 628161 dated Aug. 25, 2014.
Official Communication for U.S. Appl. No. 12/556,307 dated Oct. 1, 2013.
Official Communication for U.S. Appl. No. 12/556,307 dated Feb. 13, 2012.
Official Communication for U.S. Appl. No. 12/556,307 dated Mar. 14, 2014.
Official Communication for U.S. Appl. No. 12/556,307 dated Sep. 2, 2011.
Official Communication for U.S. Appl. No. 12/556,307 dated Jun. 9, 2015.
Official Communication for U.S. Appl. No. 13/827,491 dated Dec. 1, 2014.
Official Communication for U.S. Appl. No. 13/827,491 dated Jun. 22, 2015.
Official Communication for U.S. Appl. No. 13/827,491 dated Oct. 9, 2015.
Official Communication for U.S. Appl. No. 14/014,313 dated Jun. 18, 2015.
Official Communication for U.S. Appl. No. 14/014,313 dated Feb. 26, 2016.
Official Communication for U.S. Appl. No. 14/223,918 dated Jun. 8, 2015.
Official Communication for U.S. Appl. No. 14/304,741 dated Mar. 3, 2015.
Official Communication for U.S. Appl. No. 14/304,741 dated Aug. 6, 2014.
Official Communication for U.S. Appl. No. 14/552,336 dated Jul. 20, 2015.
Official Communication for U.S. Appl. No. 14/571,098 dated Nov. 10, 2015.
Official Communication for U.S. Appl. No. 14/571,098 dated Mar. 11, 2015.
Official Communication for U.S. Appl. No. 14/571,098 dated Feb. 23, 2016.
Official Communication for U.S. Appl. No. 14/571,098 dated Aug. 24, 2015.
Official Communication for U.S. Appl. No. 14/571,098 dated Aug. 5, 2015.
Official Communication for U.S. Appl. No. 14/800,447 dated Dec. 10, 2015.
Official Communication for U.S. Appl. No. 14/800,447 dated Mar. 3, 2016.
Ferreira et al., "A Scheme for Analyzing Electronic Payment Systems," Brasil 1997.
Gill et al., "Computerised Linking of Medical Records: Methodological Guidelines,".
Winkler, William E., "Bureau of the Census Statistical Research Division Record Linkage Software and Methods for Merging Administrative Lists," Statistical Research Report Series No. RR2001/03, Jul. 23, 2001, https://www.census.gov/srd/papers/pdf/rr2001-03.pdf, retrieved on Mar. 9, 2016.
Notice of Acceptance for Australian Patent Application No. 2014203669 dated Jan. 21, 2016.
Notice of Allowance for U.S. Appl. No. 12/556,307 dated Mar. 21, 2016.
Official Communication for European Patent Application No. 10188239.7 dated Mar. 24, 2016.
Official Communication for European Patent Application No. 14158958.0 dated Mar. 11, 2016.
Official Communication for European Patent Application No. 14158977.0 dated Mar. 11, 2016.
Official Communication for European Patent Application No. 15200073.3 dated Mar. 30, 2016.
Official Communication for European Patent Application No. 16184820.5 dated Jan. 19, 2018.
Official Communication for U.S. Appl. No. 13/827,491 dated Mar. 30, 2016.
Official Communication for U.S. Appl. No. 14/526,066 dated Jan. 21, 2016.
Official Communication for U.S. Appl. No. 14/526,066 dated May 6, 2016.
Official Communication for U.S. Appl. No. 14/800,447 dated Jun. 6, 2016.
Official Communication for U.S. Appl. No. 14/975,215 dated May 19, 2016.
Official Communication for U.S. Appl. No. 15/233,149 dated Dec. 22, 2017.

* cited by examiner

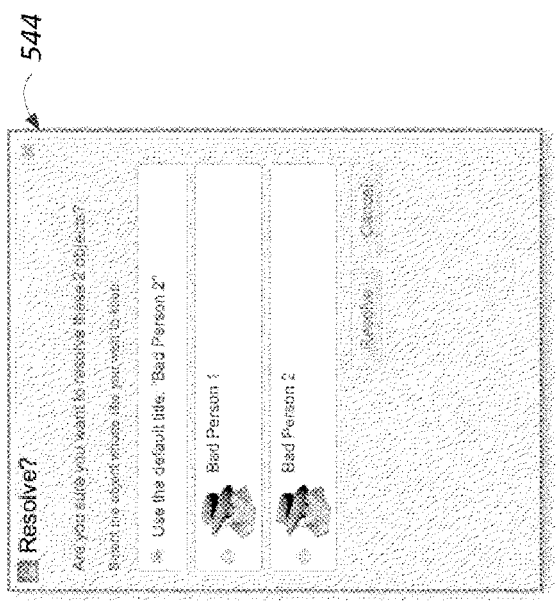
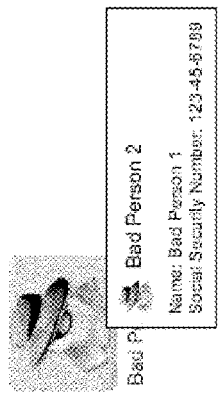
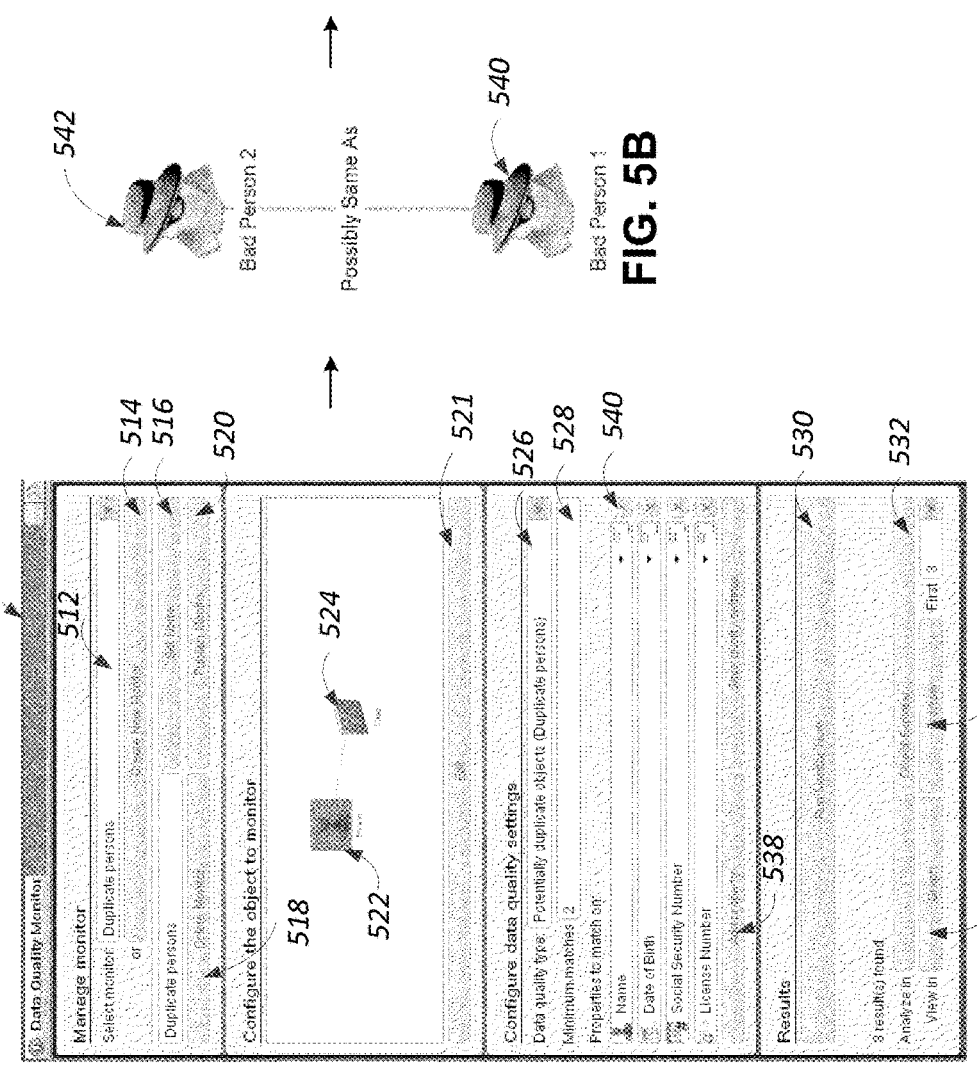
FIG. 5A, FIG. 5B, FIG. 5C, FIG. 5D

SYSTEM AND METHOD FOR DATA QUALITY MONITORS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation of Ser. No. 14/094,418, filed Dec. 2, 2013, which is a continuation of U.S. patent application Ser. No. 13/935,861 filed Jul. 5, 2013, which issued as U.S. Pat. No. 8,601,326. Each of these applications are hereby incorporated by reference herein in their entireties.

TECHNICAL FIELD

The present disclosure relates to systems and techniques for data quality monitoring. More specifically, identifying and resolving data quality issues and presenting data with potential quality issues for user confirmation and resolution.

BACKGROUND

Traditional automated data integration may result in various data quality issues. Automatic scripts to search for and resolve such data quality issues may create further data quality problems.

SUMMARY

There is a need to identify and monitor data quality problems automatically and intelligently. In accordance with one aspect, a computer system is configured to include one or more computer processors and a tangible storage device storing one or more module configured for execution by the one or more computer processors in order to: receive, by the computer system, selection of an object type to monitor for possible data quality problems; receive, by the computer system, selection of one or more data quality criterion; determine potential data quality problems by scanning data associated with a plurality of objects of the selected object type in order to determine if the selected one or more data quality criterion are matched by respective objects; generate a user interface indicating the potential data quality problems of respective objects match the selected one or more data quality criterion, and including one or more properties of the matching objects; receive from a user of the computing environment an indication of how to resolve the potential data quality problems; and implement the indicated resolution.

In some embodiments, the data quality monitor type is one of: possible duplicate objects, missing properties, multi-valued properties, unparsed properties, disallowed enumerations, numeric range violations, and date range violations. In some embodiments, the data quality monitor type is possible duplicate objects, and said determining objects having potential data quality problems further comprises identifying respective objects each having common property values for a predetermined quality of the selected one or more properties. In some embodiments, the indication of how to resolve the potential data quality problem comprises an indication of two or more objects having potential data quality problems that are duplicates; and said implementing the indicated resolution comprises combining the two or more indicated objects into a single object. In some embodiments, the one or more properties of the objects having potential data quality problems indicates a quantity of the identified respective objects sharing the selected one or more properties. In some embodiments, the data quality monitor type is missing properties; and said determining objects having potential data quality problems further comprises identifying respective objects that are missing a predetermined of the selected one or more properties.

In some embodiments, the data quality monitor type is multi-valued properties; and said determining objects having potential data quality problems further comprises identifying respective objects that have multiple values for ones of the selected one or more properties. In some embodiments, the indication of how to resolve the potential data quality problem comprises an indication of one of the multiple values that is correct; and said implementing the indicated resolution further comprises removing all of the multiple values except for the indicated one or multiple values that is correct. In some embodiments, the data quality monitor type is unparsed properties; and said determining objects having potential data quality problems further comprises identifying respective objects that have property values for one or more of the selected one or more properties including unparsed data.

In some embodiments, the data quality monitor type is disallowed enumerations; and said determining objects having potential data quality problems further comprises identifying respective objects that have property values for one or more of the selected one or more properties including disallowed enumerations. In some embodiments, the data quality monitor type is numeric range violation; and said determining objects having potential data quality problems further comprises identifying respective objects that have property values that violate an allowed numeric range for the respective selected property. In some embodiments, the data quality monitor type is date range violation; and said determining objects having potential data quality problems further comprises identifying respective objects that have property values that violate an allowed date range for the respective selected property. In some embodiments, the computer system further comprises receiving selection of one or more object types that the selected object type is required to be associated with in order to be included in the scanned plurality of objects. In some embodiments, the computer system further comprises receiving one or more Boolean operators for the selected one or more properties and/or an indication of how many of the selected one or more properties are required in order to identify the respective objects as objects having potential data quality problems.

In accordance with another aspect, a computer implemented method comprises under control of a computing system having one or more physical processors and configured to process large amounts of data, receiving, by the computing system, selection of an object type to monitor for possible data quality problems; receiving, by the computing system, selection of a data quality monitor type; receiving, by the computing system, selection of one or more properties of objects of the selected object type; determining objects having potential data quality problems by scanning data associated with a plurality of objects of the selected object type in order to locate respective objects matching the selected one or more properties; generating a user interface indicating the objects having potential data quality problems, and including one or more properties of the objects having potential data quality problems; receiving, by the computing system, an indication of how to resolve the potential data quality problems; and implementing the indicated resolution. In some embodiment, the data quality monitor type is one of: possible duplicate objects, missing properties, multi-valued properties, unparsed properties, disallowed enumerations, and numeric range violation, and date range violation. In some embodiment, the computer implemented method further comprises receiving one or more Boolean operators for the selected one or more properties and/or an indication of how many of the selected one or more properties are required in order to identify the respective objects as objects having potential data quality problems.

In accordance with another aspect, a non-transitory computer-readable storage medium storing computer-executable instructions configured to direct a computing system to: receive selection of an object type to monitor for possible data quality problems; receive selection of one or more data quality criterion; determine potential data quality problems by scanning data associated with a plurality of objects of the selected object type in order to determine if the selected one or more data quality criterion are matched by respective objects; generate a user interface indicating the potential data quality problems of respective objects; match the selected one or more data quality criterion, and including one or more properties of the matching objects; receive from a user of the computing environment an indication of how to resolve the potential data quality problems; and implement the indicated resolution. In some embodiments, the the data quality monitor type is one of: possible duplicate objects, missing properties, multi-valued properties, unparsed properties, disallowed enumerations, and numeric range violation, and date range violation. In some embodiments, the non-transitory computer-readable storage medium further comprises receiving selection of one or more object types that the selected object type is required to be associated with in order to be included in the scanned plurality of objects.

BRIEF DESCRIPTION OF THE DRAWINGS

FIG. 5A illustrates an example interface that is configured to enable users to establish criteria for a duplicate objects data quality monitor.

FIG. 5B illustrates potentially duplicate objects identified by a data quality monitor system.

FIG. 5C illustrates an example interface that is configured to enable users to review additional data related to identified potentially duplicate objects and determine whether the objects are duplicate and should be resolved.

FIG. 5D illustrates an example user interface wherein potentially duplicate objects are resolved and results of the resolution are displayed.

DETAILED DESCRIPTION OF CERTAIN EMBODIMENTS

Definitions

Figure 1:
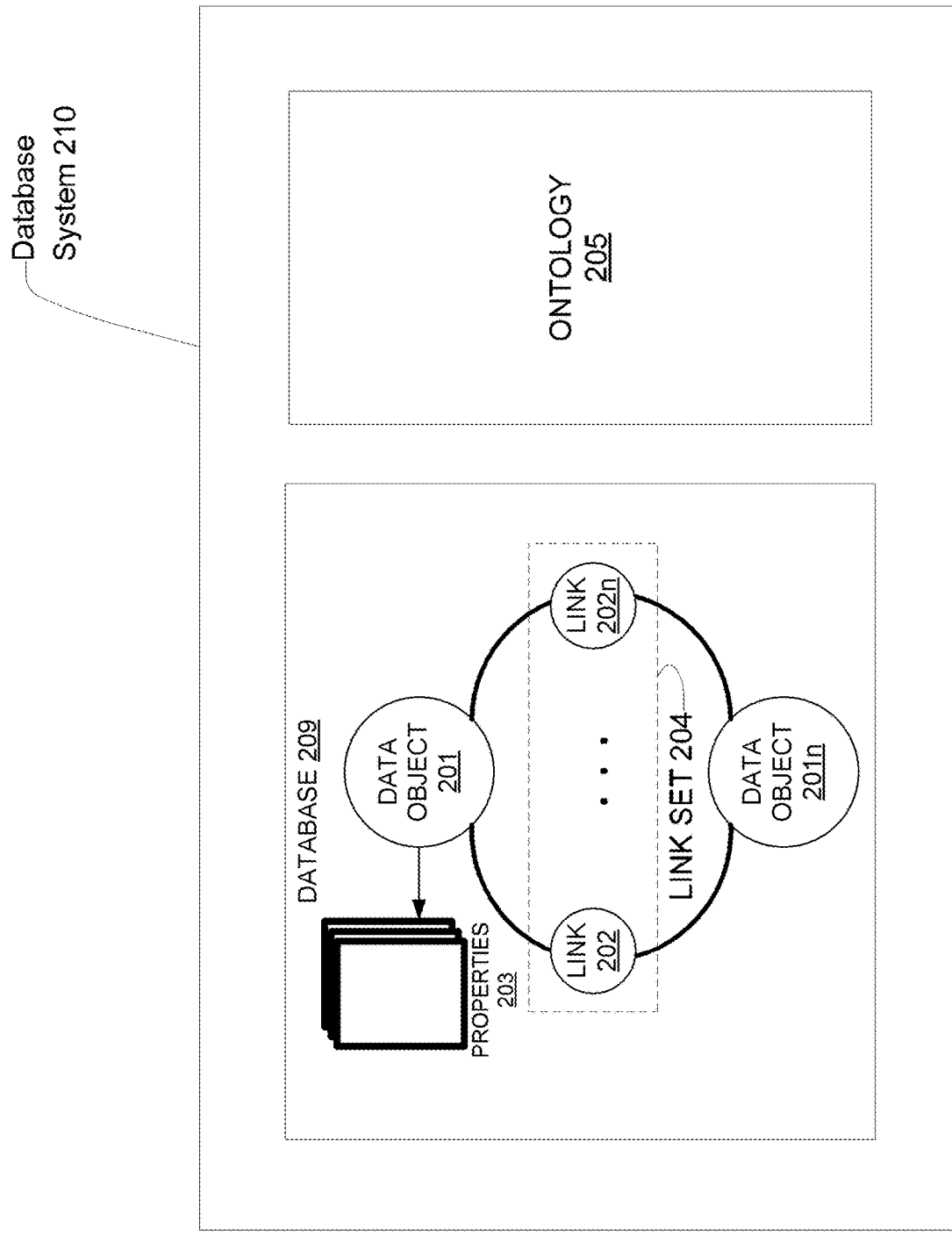
FIG. 1 illustrates one embodiment of a database system using an ontology.

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Ontology: Stored information that provides a data model for storage of data in one or more databases. For example, the stored data may comprise definitions for object types and property types for data in a database, and how objects and properties may be related.

Database: A broad term for any data structure for storing and/or organizing data, including, but not limited to, relational databases (Oracle database, mySQL database, etc.), spreadsheets, XML files, and text file, among others.

Data Object or Object: A data container for information representing specific things in the world that have a number of definable properties. For example, a data object can represent an entity such as a person, a place, an organization, a market instrument, or other noun. A data object can represent an event that happens at a point in time or for a duration. A data object can represent a document or other unstructured data source such as an e-mail message, a news report, or a written paper or article. Each data object may be associated with a unique identifier that uniquely identifies the data object. The object's attributes (e.g. metadata about the object) may be represented in one or more properties.

Object Type: Type of a data object (e.g., person, event, or document). Object types may be defined by an ontology and may be modified or updated to include additional object types. An object definition (e.g., in an ontology) may include how the object is related to other objects, such as being a sub-object type of another object type (e.g. an agent may be a sub-object type of a person object type), and the properties the object type may have.

Properties: Attributes of a data object that represent individual data items. At a minimum, each property of a data object has a property type and a value or values.

Property Type: The type of data a property is, such as a string, an integer, or a double. Property types may include complex property types, such as a series data values associated with timed ticks (e.g. a time series), etc.

Property Value: The value associated with a property, which is of the type indicated in the property type associated with the property. A property may have multiple values.

Link: A connection between two data objects, based on, for example, a relationship, an event, and/or matching properties. Links may be directional, such as one representing a payment from person A to B, or bidirectional.

Link Set: Set of multiple links that are shared between two or more data objects.

Data Quality Monitors: rules including one or more criterion configured to identify potential data quality problems in data objects or between multiple data objects. Actions to confirm possibly data quality problems and/or correct such data quality problems may be taken by a user or by automatic processes.

Object Centric Data Model

To provide a framework for the following discussion of specific systems and methods described herein, an example database system 210 using an ontology 205 will now be described. This description is provided for the purpose of providing an example and is not intended to limit the techniques to the example data model, the example database system, or the example database system's use of an ontology to represent information.

In one embodiment, a body of data is conceptually structured according to an object-centric data model represented by ontology 205. The conceptual data model is independent of any particular database used for durably storing one or more database(s) 209 based on the ontology 205. For example, each object of the conceptual data model may correspond to one or more rows in a relational database or an entry in Lightweight Directory Access Protocol (LDAP) database, or any combination of one or more databases.

FIG. 1 illustrates an object-centric conceptual data model according to an embodiment. An ontology 205, as noted above, may include stored information providing a data model for storage of data in the database 209. The ontology 205 may be defined by one or more object types, which may each be associated with one or more property types. At the highest level of abstraction, data object 201 is a container for information representing things in the world. For example, data object 201 can represent an entity such as a person, a place, an organization, a market instrument, or other noun. Data object 201 can represent an event that happens at a point in time or for a duration. Data object 201 can represent a document or other unstructured data source such as an e-mail message, a news report, or a written paper or article. Each data object 201 is associated with a unique identifier that uniquely identifies the data object within the database system.

Different types of data objects may have different property types. For example, a "person" data object might have an "Eye Color" property type and an "Event" data object might have a "Date" property type. Each property 203 as represented by data in the database system 210 may have a property type defined by the ontology 205 used by the database 209.

Objects may be instantiated in the database 209 in accordance with the corresponding object definition for the particular object in the ontology 205. For example, a specific monetary payment (e.g., an object of type "event") of US$30.00 (e.g., a property of type "currency") taking place on Mar. 27, 2009 (e.g., a property of type "date") may be stored in the database 209 as an event object with associated currency and date properties as defined within the ontology 205.

The data objects defined in the ontology 205 may support property multiplicity. In particular, a data object 201 may be allowed to have more than one property 203 of the same property type. For example, a "person" data object might have multiple "Address" properties or multiple "Name" properties.

Each link 202 represents a connection between two data objects 201. In one embodiment, the connection is either through a relationship, an event, or through matching properties. A relationship connection may be asymmetrical or symmetrical. For example, "person" data object A may be connected to "person" data object B by a "Child Of" relationship (where "person" data object B has an asymmetric "Parent Of" relationship to "person" data object A), a "Kin Of" symmetric relationship to "person" data object C, and an asymmetric "Member Of" relationship to "Organization" data object X. The type of relationship between two data objects may vary depending on the types of the data objects. For example, "person" data object A may have an "Appears In" relationship with "Document" data object Y or have a "Participate In" relationship with "Event" data object E. As an example of an event connection, two "person" data objects may be connected by an "Airline Flight" data object representing a particular airline flight if they traveled together on that flight, or by a "Meeting" data object representing a particular meeting if they both attended that meeting. In one embodiment, when two data objects are connected by an event, they are also connected by relationships, in which each data object has a specific relationship to the event, such as, for example, an "Appears In" relationship.

As an example of a matching properties connection, two "person" data objects representing a brother and a sister, may both have an "Address" property that indicates where they live. If the brother and the sister live in the same home, then their "Address" properties likely contain similar, if not identical property values. In one embodiment, a link between two data objects may be established based on similar or matching properties (e.g., property types and/or property values) of the data objects. These are just some examples of the types of connections that may be represented by a link and other types of connections may be represented; embodiments are not limited to any particular types of connections between data objects. For example, a document might contain references to two different objects. For example, a document may contain a reference to a payment (one object), and a person (a second object). A link between these two objects may represent a connection between these two entities through their co-occurrence within the same document.

Each data object 201 can have multiple links with another data object 201 to form a link set 204. For example, two "person" data objects representing a husband and a wife could be linked through a "Spouse Of" relationship, a matching "Address" property, and one or more matching "Event" properties (e.g., a wedding). Each link 202 as represented by data in a database may have a link type defined by the database ontology used by the database.

Figure 2:
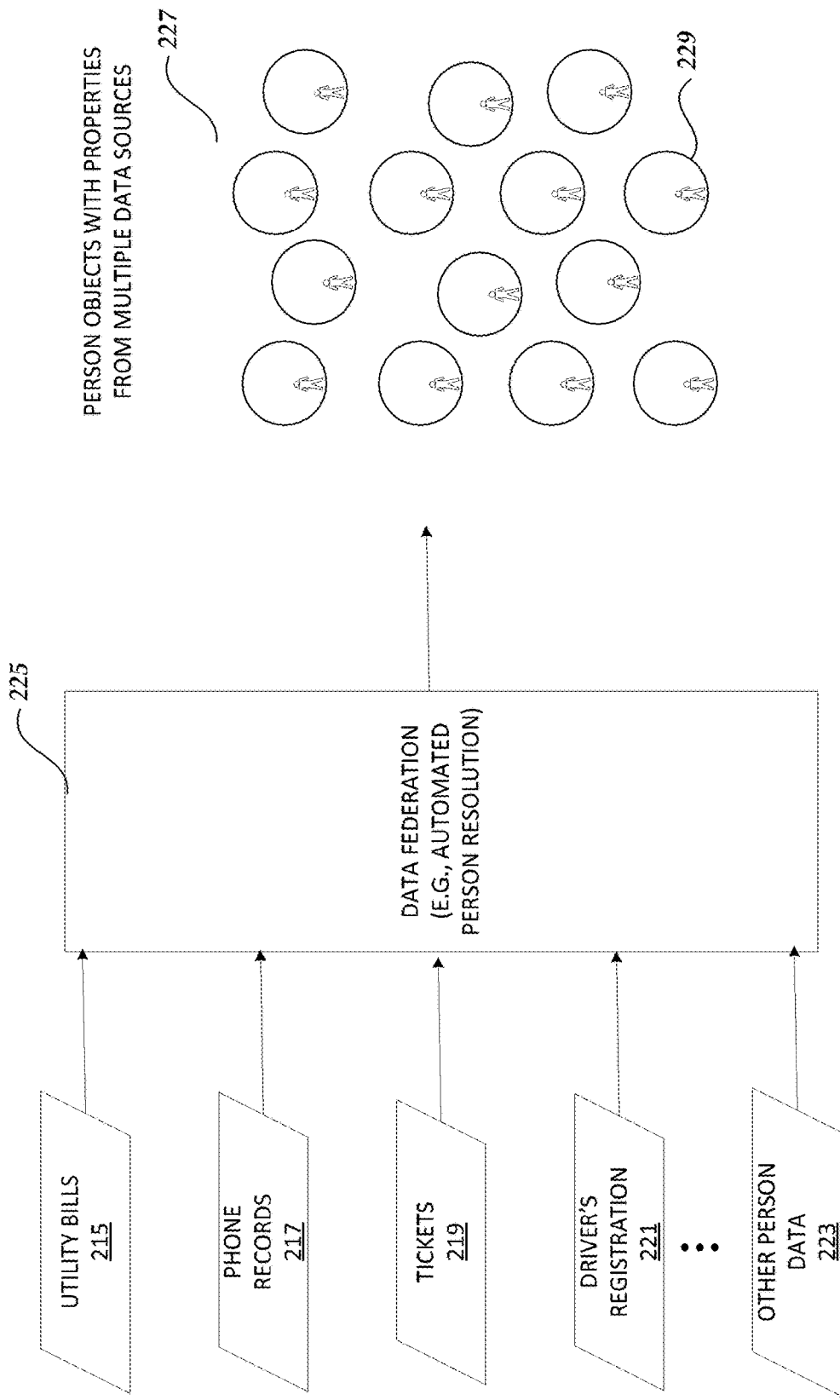
FIG. 2 illustrates one embodiment of a process of generating person objects with properties from multiple data sources.

FIG. 2 illustrates one embodiment of a process of generating person objects with properties from multiple data sources. Problems related to data quality may arise in certain of the person data objects as a result of the automatic integration of data from multiple sources. Additionally, errors may be introduced by data entry mistakes, such as typographical errors, and/or in other manners. In the example of FIG. 2, multiple data sources provide data to the data federation system 225 including utility bills 215, phone records 217, tickets 217, driver's registration 221, and other personal data 223, etc. Depending on the embodiment, the data sources that provide these various types of data may be different entities or a single entity.

Each data record (e.g., data provided about a person from one of the data sources) may include information about one or more persons, and properties of person objects from the various data sources may vary. For example, the utility bills data 215 may include properties such as name, address, account number, amount due, past utility usage information, past payment history, and/or minimum amount due, while the phone records data 217 may include information such as name, address, phone number(s) and/or account number(s) (which may or may not be the same as phone number), amount due, usage information, past payment history, minimum amount due, phone calls placed, message sent, recipient's information (phone number), information about each phone call placed and/or each message sent, for example. The tickets data 219 may include information such as name of a driver, address, phone number, driver license number, vehicle registration number, event involved, ticket type, and/or date of the ticket. The driver's registration data 221 may include information such as name, date of birth, height, weight, eye color, hair color, date license issued, and/or expiration date.

In some embodiments, through data federation system 225, data from various sources may be automatically federated to create multiple person objects 227. For example, the utility bills data 215 of a person may show that the person lives at 123 Oak Street, and his phone number is 123-456-7890. The same person's phone records data 217 may show that he lives at 789 Willow Road and his phone number is 098-765-4321. The person's tickets data 219 may show that this person lives at 123 Oak Street, his gender is "female," he was born on 01/13, and his phone number is 098-765-4321. Finally, the person's driver's registration 221 may show that he lives at 789 Willow Road, he was born on Jan. 13, 1967, his gender is "male," and his phone number is 123-456-7890.

In this example, the data federation system 225 may update the corresponding person object (or create the person object if one doesn't already exist) using some automated data federation rules and processes. In some embodiments, the end result of the data federation process may be something that simply takes all the source information and compiles it together in the person object. For example, if the data federation process integrates the data from various sources directly without any changes, the person may be indicated as having two genders: male and female. The person may also be shown as having two birth dates: "01/13" and "Jan. 13, 1967." Furthermore, the first birth date of "01/13" may be interpreted as January 2013 instead of January 13$^{th}$ of a year.

Accordingly, due to data quality issues, the federated data through the data federation system 225 may involve all kinds of discrepancies, missing values, and other types of potential problems. These problems may sometimes be difficult to recognize such that the problems may be corrected.

Figure 3:
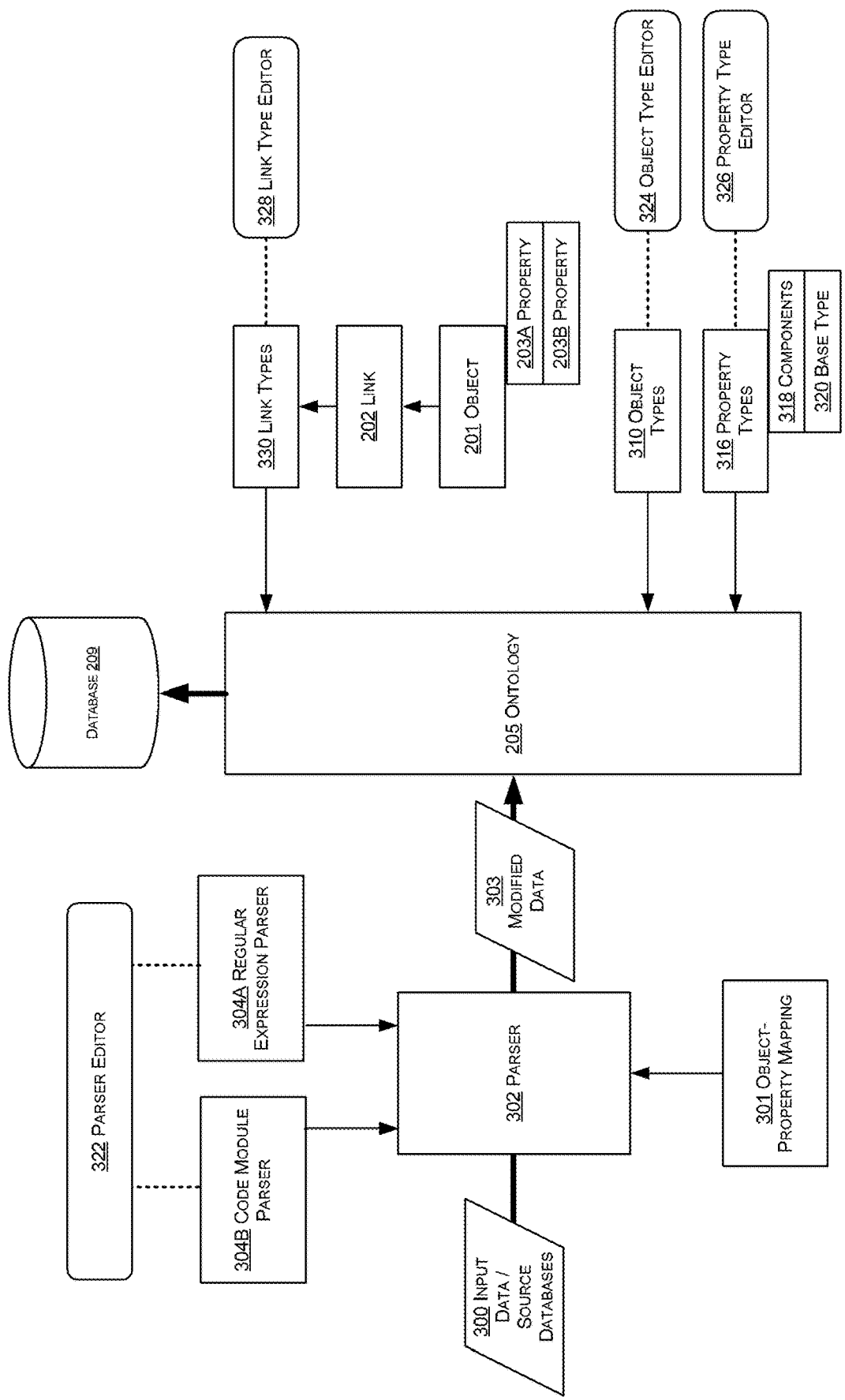
FIG. 3 illustrates one embodiment of a system for creating data in a data store using a dynamic ontology.

FIG. 3 is a block diagram illustrating exemplary components and data that may be used in identifying and storing data according to an ontology. In this example, the ontology may be configured, and data in the data model populated, by a system of parsers and ontology configuration tools. In the embodiment of FIG. 3, input data 300 is provided to parser 302. The input data may comprise data from one or more sources, such as data sources that provide the various data items discussed with reference to FIG. 2. For example, an institution may have one or more databases with information on credit card transactions, rental cars, and people. The databases may contain a variety of related information and attributes about each type of data, such as a "date" for a credit card transaction, an address for a person, and a date for when a rental car is rented. The parser 302 is able to read a variety of source input data types and determine which type of data it is reading.

In accordance with the discussion above, the example ontology 205 comprises stored information providing the data model of data stored in database 209, and the ontology is defined by one or more object types 310, one or more property types 316, and one or more link types 330. Based on information determined by the parser 302 or other mapping of source input information to object type, one or more data objects 201 may be instantiated in the database 209 based on respective determined object types 310, and each of the objects 201 has one or more properties 203 that are instantiated based on property types 316. Two data objects 201 may be connected by one or more links 202 that may be instantiated based on link types 330. The property types 316 each may comprise one or more base types 320, such as a string, number, etc. In some embodiments, property types include only a base type of string, number, date, enumeration, or composite. Depending on the embodiment, property types may or may not have a hierarchical structure like objects do. For instance, a missing child object type can be a sub-type of the person object type, but a home property type cannot be a sub-type of a location property type.

In some embodiments, composite property types contain multiple components, but may still be considered a single property. For instance, an Address property may be a composite property, formed from multiple components, such as Address 1 (string), Address 2 (string), City (string), State (string), and ZIP (could be number or a string).

In some embodiments, the ontology rules may also restrict which properties are allowed on which objects, as well as what link relationships are allowed between objects.

In an embodiment, a user of the system uses an object type editor 324 to create and/or modify the object types 310 and define attributes of the object types. In an embodiment, a user of the system uses a property type editor 326 to create and/or modify the property types 316 and define attributes of the property types. In an embodiment, a user of the system uses link type editor 328 to create the link types 330. Alternatively, other programs, processes, or programmatic controls may be used to create link types and property types and define attributes, and using editors is not required.

In an embodiment, creating a property type 316 using the property type editor 326 involves defining at least one parser definition using a parser editor 322. In some embodiments, a parser definition comprises metadata that informs parser 302 how to parse input data 300 to normalize the value assigned to the property type 316 that is associated with the parser definition. For example, the ontology parser may determine how to convert both inputs "Jan. 1, 2002" and "Jan. 1, 2002" into a normalized value "2002-01-01 00:00."

Depending on the embodiment, a composite property parser may identify individual components. For example, a composite parser for may turn an address "111 Main St., New City, ST, 12345" into normalized values such as: Address 1: 111 Main St; City: New City; State: ST; Zip: 12345. In some embodiments, if parsing rules fail, the original value may be kept in an unparsed format. This may be later identified as a potential data quality issue by a data quality monitor. In some embodiments, code parsers may choose which property type to use. In some embodiments, the code may map a data column from the input to a property type in the ontology and then parse the input.

In an embodiment, each parser definition may comprise a regular expression parser 304A or a code module parser 304B. In other embodiments, other kinds of parser definitions may be provided using scripts or other programmatic elements. Once defined, both a regular expression parser 304A and a code module parser 304B can provide input to parser 302 to control parsing of input data 300.

Using the data types defined in the ontology, input data 300 may be parsed by the parser 302 determine which object type 310 should receive data from a record created from the input data, and which property types 316 should be assigned to data from individual field values in the input data. Based on the object-property mapping 301, the parser 302 selects one of the parser definitions that is associated with a property type in the input data. The parser parses an input data field using the selected parser definition, resulting in creating new or modified data 303. The new or modified data 303 is added to the database 209 according to ontology 205 by storing values of the new or modified data in a property of the specified property type. As a result, input data 300 having varying format or syntax can be created in database 209. The ontology 205 may be modified at any time using object type editor 324, property type editor 326, and link type editor 328, or under program control without human use of an editor. Parser editor 322 enables creating multiple parser definitions that can successfully parse input data 300 having varying format or syntax and determine which property types should be used to transform input data 300 into new or modified input data 303.

Figure 4A:
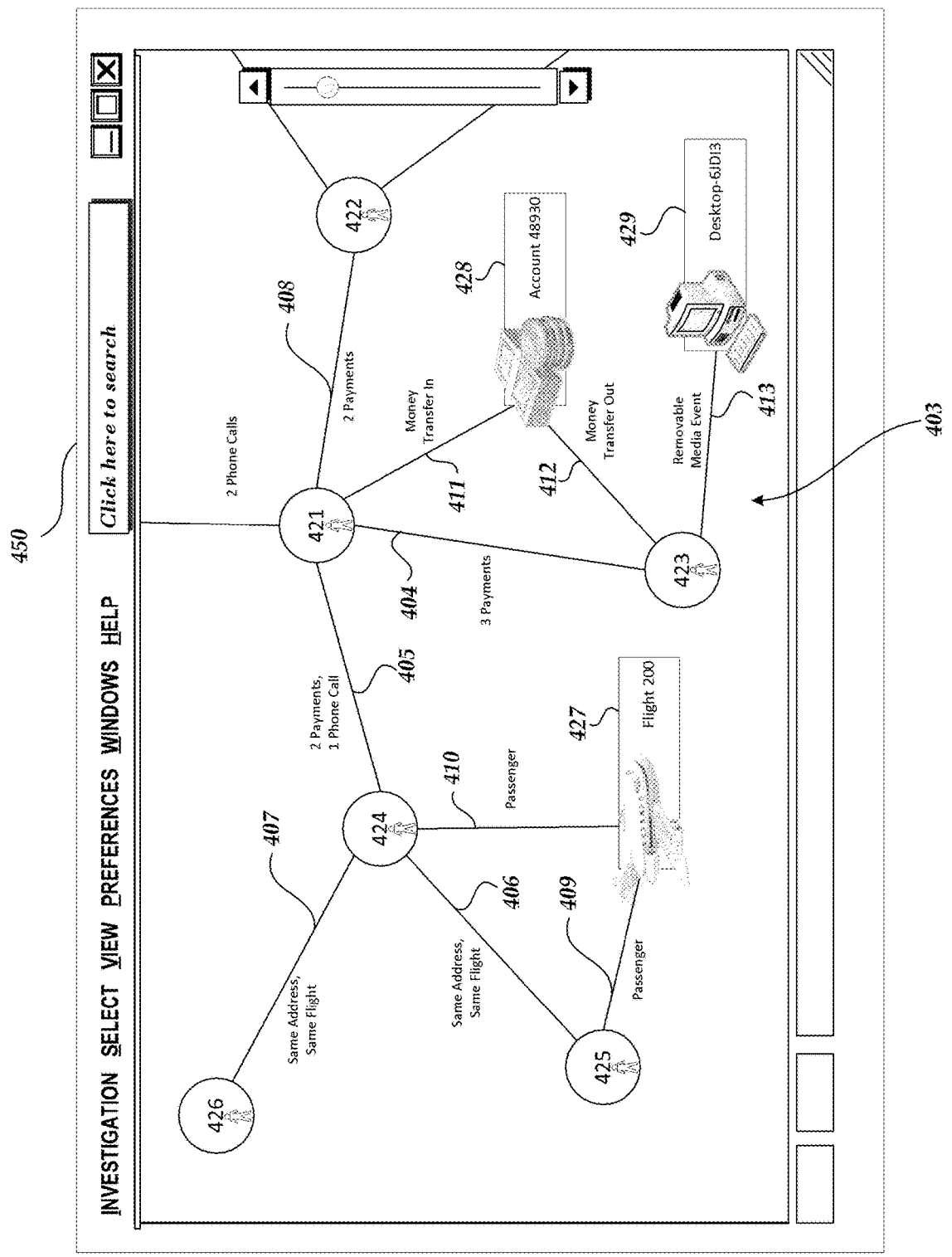
FIG. 4A illustrates a sample user interface using relationships described in a data store using a dynamic ontology.

The properties, objects, and the links (e.g. relationships) between the objects can be visualized using a graphical user interface (GUI). For example, FIG. 4A displays a user interface showing a graph representation 403 of relationships (including relationships or links 404, 405, 406, 407, 408) between the data objects (including data objects 421, 422, 423, 424, 425, 426) that are represented as nodes in the example of FIG. 4. In this embodiment, data objects 421-426 are person objects, such as the person objects 227 discussed with reference to FIG. 2. In this example, the person nodes (associated with person data objects) may have relationships to other person nodes, for example, through payment objects. For example, relationship 404 is based on a payment associated with the individuals indicated in person data objects 421 and 423. The link 404 represents these shared payments (for example, the individual associated with data object 411 may have paid the individual associated with data object 413 on three occasions). These relationships may be stored as links, or in some embodiments, as properties, where a relationship may be detected between the properties, or as event objects. In some cases, as stated above, the links may be directional. For example, a payment link may have a direction associated with the payment, where one person object is a receiver of a payment, and another person object is the payer of payment.

In addition to visually showing relationships between the data objects, the user interface may allow various other manipulations. For example, the objects within database 209 may be searched using a search interface 450 (e.g., text string matching of object properties), inspected (e.g., properties and associated data viewed), filtered (e.g., narrowing the universe of objects into sets and subsets by properties or relationships), and statistically aggregated (e.g., numerically summarized based on summarization criteria), among other operations and visualizations.

Figure 4B:
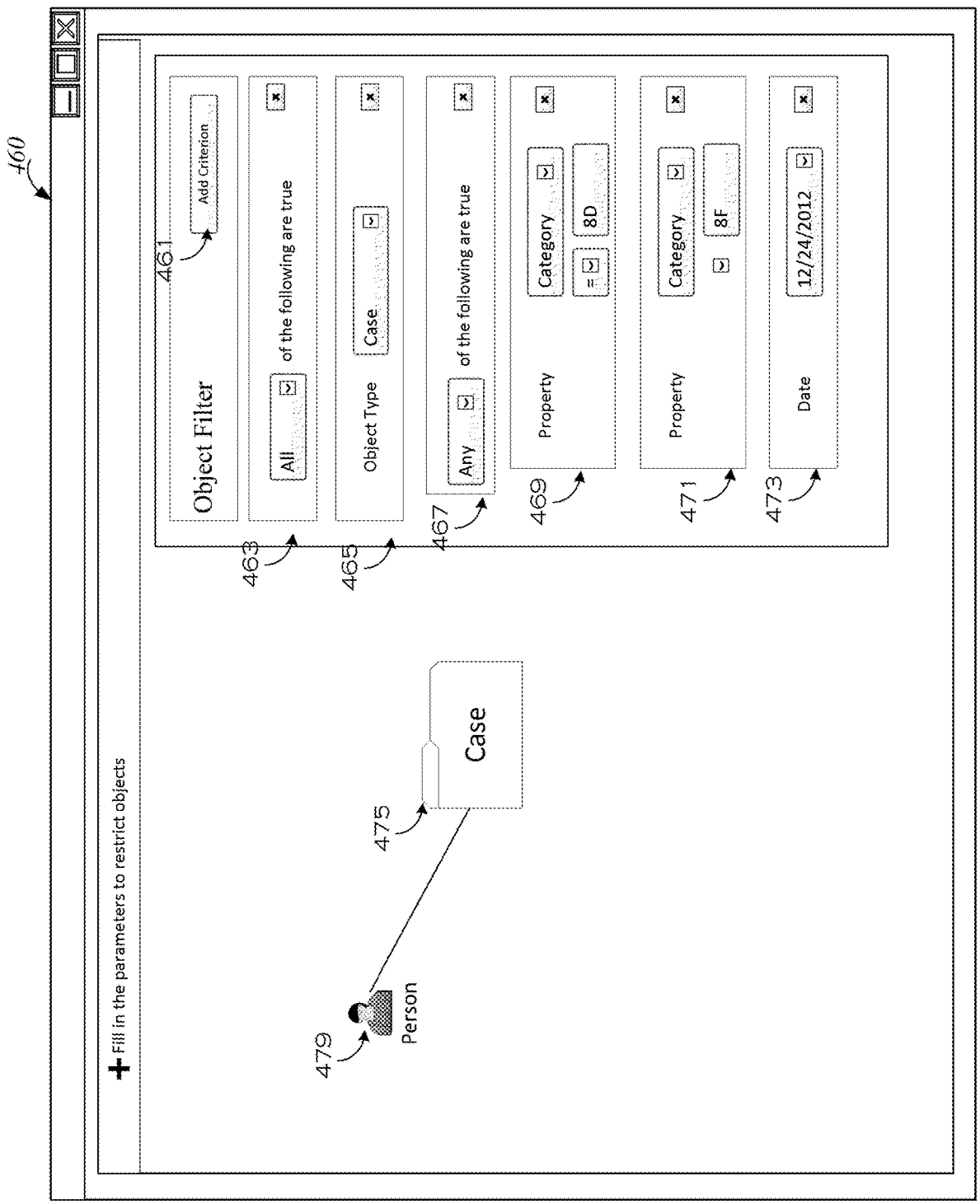
FIG. 4B illustrates a user interface that is configured to receive user-selected criteria for a data quality monitor, according to one embodiment.

FIG. 4B illustrates an object filter user interface 460 that is configured to receive user-selected criteria for a data quality monitor and display results given the criteria, according to an embodiment of the present disclosure.

In the embodiment of FIG. 4B, the object filter initially receives from the user a selection of one or more types of objects to be monitored. In this example, the selected object type is "Case," and therefore case objects satisfying the specified criteria are displayed. In general, a case is an object type that refers to multiple other objects of possibly multiple object types. A case object may refer to various types of information, such as a case related to a criminal investigation, a case of West Nile virus infection, a case involving litigants, or a case related to economic analysis. Depending on specific user requirements, a case object may include various properties such as names of people involved, dates of events, address, phone number, outcome, etc., and a case object may be associated with multiple other object types, such as one or more person objects, event objects, etc. In some other embodiments, other object types may be selected, such as person, event, vehicle, etc.

In this example, criterion (e.g., required object types or values of properties) to be included in the data quality monitor can be added by clicking the add criterion button 461. For example, the monitor may initially include no criterion (or possibly default criterion in one embodiment), and the user adds a first criterion 469 by clicking on the add criterion button 461, and subsequently adds the criterion 471 and 473 by clicking on the add criterion button 461 additional times.

The user interface of FIG. 4B allows the user to select Boolean operators to further define requirements of the monitor. For example, the user has indicated in interface 463 that the object type is required to be a "case" and has indicated in interface 465 that any one of the listed criterion 469, 471, 473 is sufficient for a match. In one embodiment, these interfaces 463, 467 also allow the user to indicate a minimum number of the criterion that must be met, rather than the indicated "any" (in interface 467) or "all" (in interface 463). In other embodiments, relationships between the criteria may be provided in other manners.

As shown in FIG. 4B, criterion may reference any available properties of the selected object type. For example, the criteria of "category =8D" is selected in criterion 469 and "category =8F" is selected in criterion 471, while criterion 473 refers to a particular date. A user may define any additional or different criterion based on any other properties of the objects to be monitored, such as location =Boston, Mass., airline =Southwest, date range=Feb. 14, 2009 to Mar. 9, 2011, etc.

In some embodiments, a data quality monitor may be configured to restrict selected objects to objects connected to one or more specific object or objects connected to one or more type of objects. For example, if "person" is an object type that is already selected, a user may add an icon representing an object type (such as "case" 475) next to the "person" object type 479, and add a link between the two object types. With the added link between the case object 475 and the person object 479, the monitor is configured to select only case objects that are also connected to a person object. This feature may be useful to further limit the scope of searched objects. For example, if a user is only interested in case objects connected to a known criminal A, in addition to satisfying the criteria on the right side of the panel, the selected case objects are also related to the criminal A.

Data Quality Monitors

FIG. 5A illustrates an example user interface 510 that is configured to enable users to establish criteria for a data quality monitor. Initially, the user may select an existing monitor (such as a monitor that was previously generated by the user and/or another user) using the drop-down menu 512. Alternatively, the user can create a new monitor by selecting create new monitor button 514. If the user creates a new monitor, the example user interface 510 allows the user to provide a custom name, such as "Duplicate persons" by inputting the name in a text box. In addition, in some embodiments, the user interface 510 may allow the user to publish a custom monitor by clicking the publish monitor button 520, which makes the monitor available to other users (e.g., via the select monitor drop-down menu 512) such as to perform the same data quality monitoring on other datasets.

In the embodiment of FIG. 5A, the user can select one or more particular object types to monitor. In this example, person objects 522 relating to case objects 524 are configured to be monitored by this data quality monitor. A user may further edit the objects to monitor by clicking the "edit" button 521, which opens a user interface such as the interface shown in FIG. 4B. In some embodiments, this may mean that person objects being monitored should be related to one or more case object, and person objects not related to any case objects should not be monitored. In some embodiments, only person objects 522 may be configured to be monitored without the additional requirement that the person objects 522 should be related to one or more case objects 524.

In this example, the user has selected a duplicate objects data quality monitor using the monitor type drop-down menu 526. Data quality monitor types may be directed to other data quality issues, such as such as missing values, unparsed properties, numeric range violations, properties with values that do not match allowed enumerations, and other types of potential data quality issues, which may also be available in the menu 526. The user interface 510 further provides a list of available property types associated with the chosen object type (in this example, person object type) for which the monitor will search.

Furthermore, the data quality monitor may also be configured to allow a user to input a number of minimum matches among the provided property criteria that result in a matching person object (or other object type in other implementations). For example, if a user has specified 4 properties and a minimum match of 2 (as shown in the example of FIG. 5A), matching at least two of the specified properties between two person objects would be deemed sufficient for identifying those two objects as potentially duplicate objects. In the example of FIG. 5A, the following properties are selected to be matched on: name, date of birth, Social Security Number, and license number.

In some embodiments, the properties to match on in order to determine whether objects are duplicate may be added or deleted. A user may click "Add property" button 538 to add additional properties. A user may also click on the remove property icon 540 next to a property to remove that property. Property settings may also be saved with the monitor.

In the embodiment of FIG. 5A, results of the data quality monitor 510 may be obtained by clicking on the "Run Monitor Now" button 530. Depending on the embodiment and the specific dataset used, duplicate objects may or may not be found according to the established data quality monitor criteria. In this example, 3 groups of person objects are found to be possible duplicates according to the specified criteria. Depending on the embodiment, results of the data quality monitor may be viewed in a graph setting by selecting 534, or in a browser setting by selecting 536.

FIG. 5B illustrates potentially duplicate objects identified by the data quality monitor defined in user interface 510 of FIG. 5A. In this example, two person objects, Bad Person 1 540 and Bad Person 2 542 are identified by the "Duplicate persons" data quality monitor as possibly the same as each other. In some embodiments where there are many objects identified, the objects may be displayed in a graph view or in a browser view with fewer objects shown at first. A user will be given the choice to drill-down, drill-up, and/or otherwise explore the identified objects.

Figure 8A:
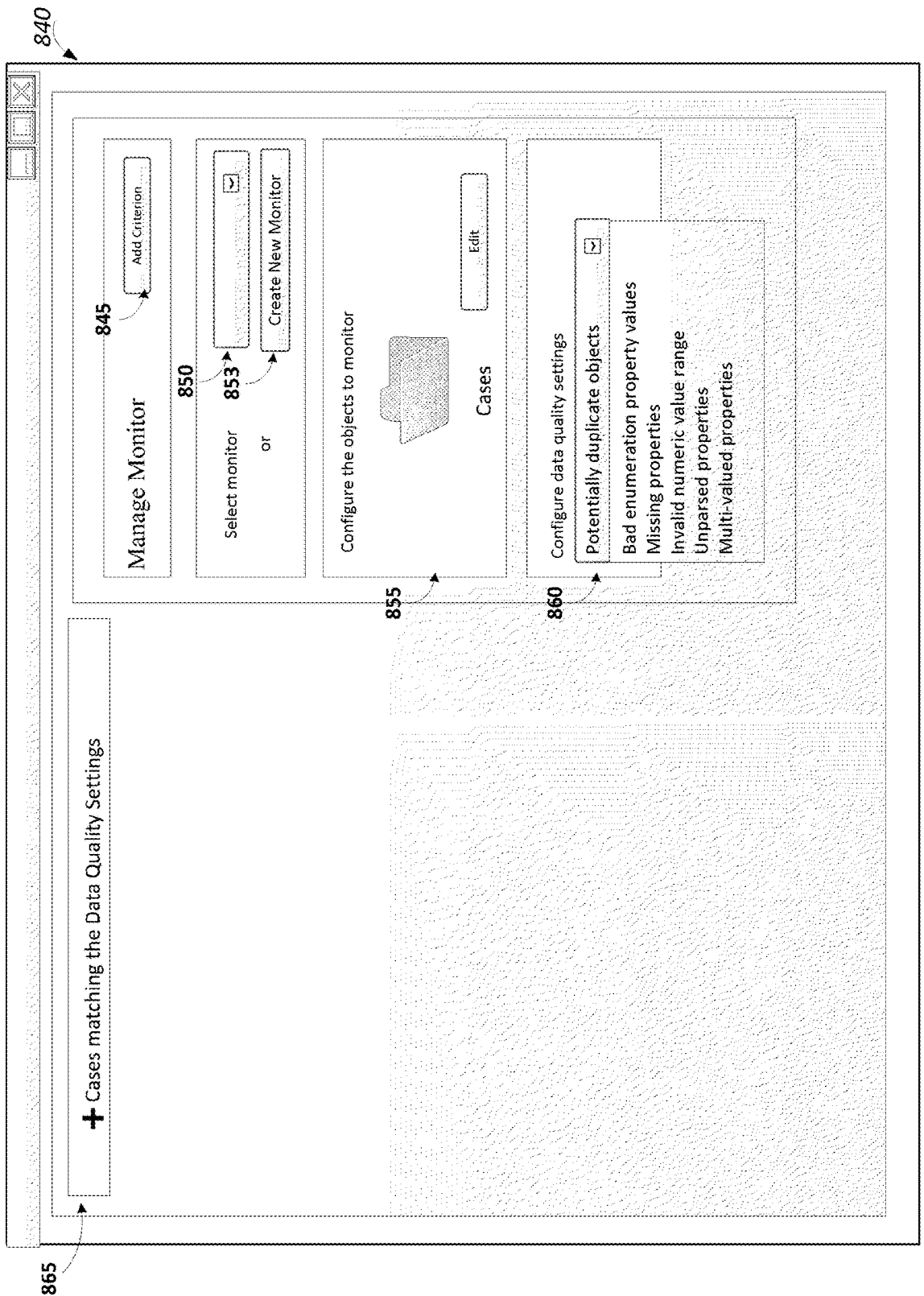
FIG. 8A illustrates an example user interface that allows a user to select criteria for a data quality monitor.
Figure 8B:
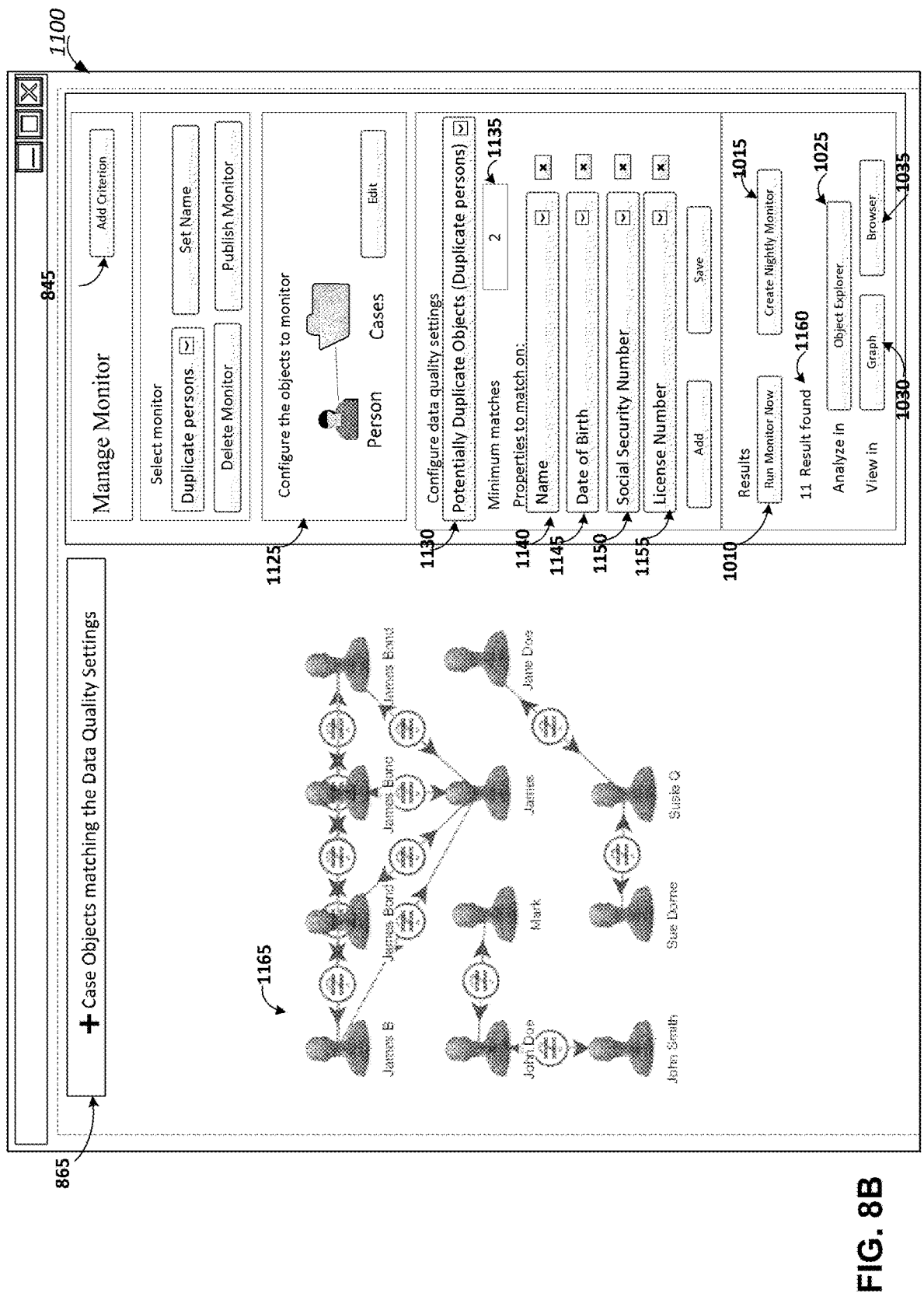
FIG. 8B illustrates another example user interface wherein a user has configured a potentially duplicate person monitor to search on both person objects and case objects.
Figure 8C:
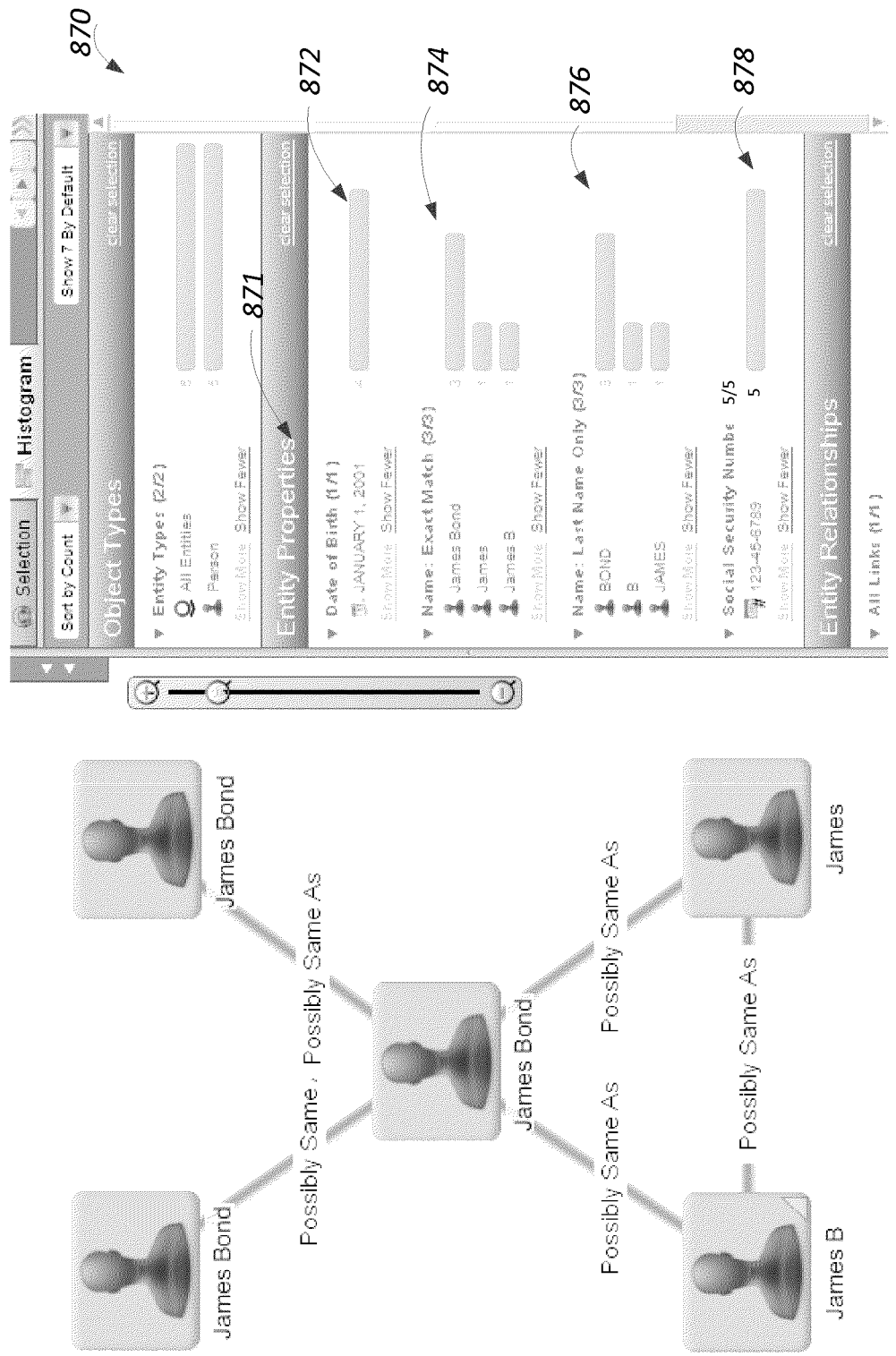
FIG. 8C illustrates an example user interface wherein a group of possibly duplicate person objects are displayed and properties of these person objects are shown.

FIG. 5C illustrates an example interface 544 that is configured to enable users indicate whether the objects are duplicate and should be resolved, possibly after reviewing additional data related to identified potentially duplicate objects (see FIG. 8C, for example). In some embodiments, a different interface may be presented for resolving groups of potentially duplicate objects. In the example interface 544, a user may be presented with a question such as "Are you sure you want to resolve these 2 objects?" In some other embodiments, a similar or different question may be asked to communicate to the user that a choice may be made to resolve the potential data quality issue. In this example, a user may choose the default title "Bad Person 2." If this choice is made, the title of the new merged objects is Bad Person 2. In this embodiment, the data on both Bad Person 1 and Bad Person 2 are merged to form the new merged object titled Bad Person 2.

In some embodiments, when a potential data quality issue is resolved, the merged object is maintained in the data store and the individual objects used to create it no longer show up separately in searches. In some embodiments, the user that initiates object resolution may also indicate that the resolution should be effective only in data accessed by the particular user and/or a particular group of user. Thus, the resolution (and/or other changes to data objects) may be selectively pushed out to other users.

FIG. 5D illustrates an example user interface 546 wherein potentially duplicate objects are resolved and results of the resolution are displayed. In this example, Bad Person 2 is found to be a potentially duplicate of some other objects. Information regarding properties of Bad Person 2, which now include properties of Bad Person 1 that was resolved into Bad Person 2, may be displayed. In some embodiments, only information that is actually used to match duplicate objects or identify other potentially data quality issues is displayed. In some other embodiments, all or relevant properties of a selected object may be displayed to a user. In this example, Bad Person 2 is show to have the name of "Bad Person 1" and a Social Security Number of 123-45-6789.

Figure 6:
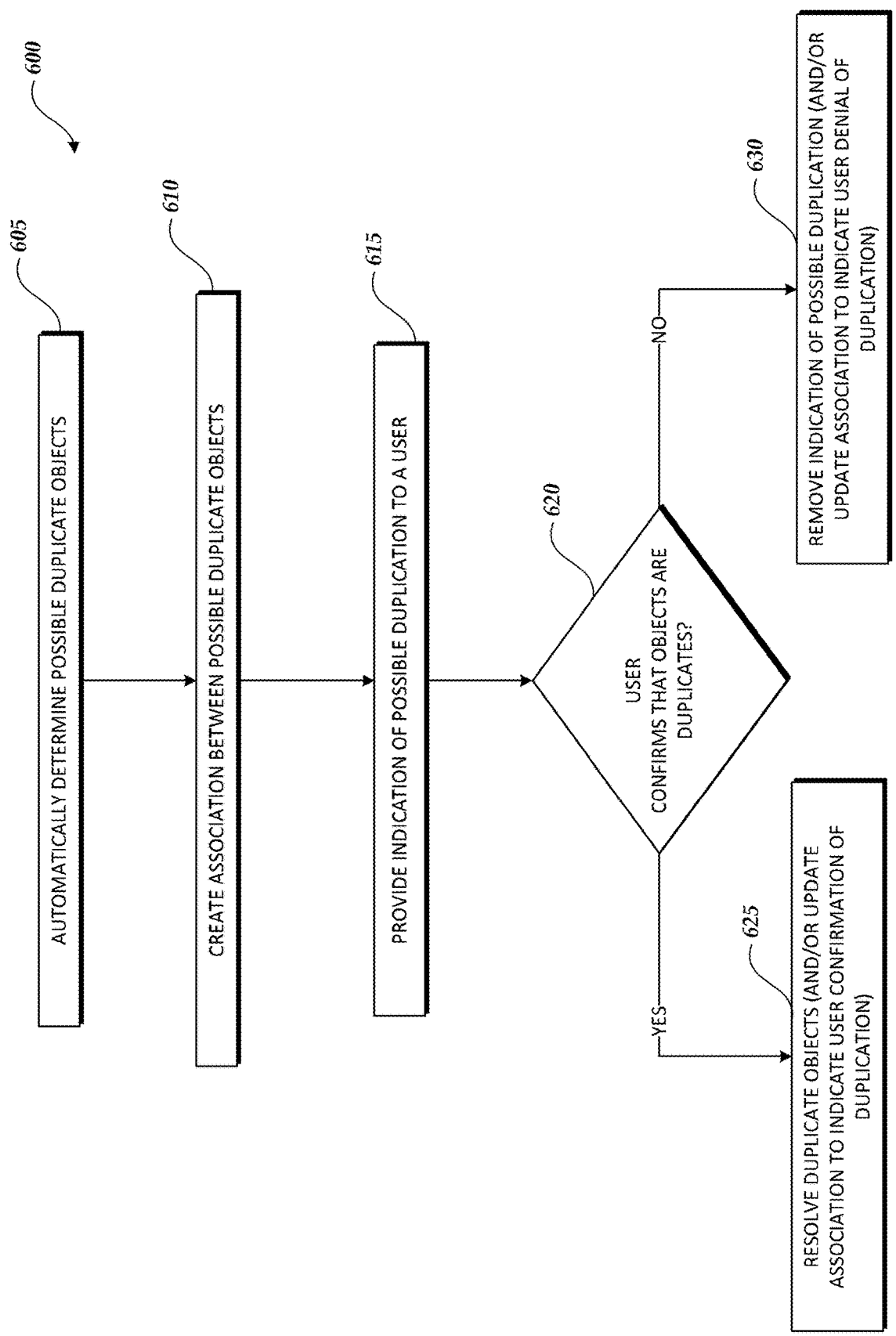
FIG. 6 is a flowchart depicting an illustrative operation of identifying, confirming, and removing or resolving duplicate objects.

FIG. 6 is a flowchart depicting an illustrative operation of identifying, confirming, and removing or resolving duplicate objects according to one embodiment. The method of FIG. 6 may be performed by a computing system used by an analyst (or other user), one or more server systems that store the object ontology (e.g., database system 210 of FIG. 1), and/or any other suitable computing system.

The method 600 begins at block 605, where a data quality monitor automatically determines possible duplicate objects based on a set of criteria (e.g., those set in user interface 510 of FIG. 5A). In some embodiments, the set of criteria may be created by a user. In some other embodiments, the set of criteria may have been already created before (e.g., by the same user, another user, or as a system default) and stored in the data quality monitor. The set of criteria may include property criteria, such as the properties to match and the minimum number of properties that needs to be matched. While a possible duplicates data quality monitor is discussed with reference to FIG. 6, other types of monitors may be executed in a similar manner. As discussed above, the other types of data quality monitors may include missing values, unparsed properties, numeric range violations, properties with values that do not match allowed enumerations, and other types of potential data quality issues.

The method 600 proceeds to block 610, where the data quality monitor creates associations between possible duplicate objects. For example, if two person objects are deemed to be possible duplicates of each other based on identical Social Security Number (SSN) and identical date of birth (DOB) (where SSN and DOB are selected properties to be matched on and the monitor requires 2 or less matching properties), a "possible duplicate objects" association/link between these two person objects may be created. In some situations, the two person objects may have some other properties that are not identical, such as different eye colors.

In another example, if four Ticket objects have the same date of issuance, name, incident type, driver's license number, and vehicle license numbers, the data quality monitor may deem them to be potentially duplicates (based on the established monitor criteria) and create associations/links between the four Ticket objects, identifying them as potential duplicates.

At block 615, the data quality monitor provides an indication of possible duplicate objects to a user. In some embodiments, the indication that some objects may potentially be duplicates of each other may be presented in a graph view, wherein the one or more identified objects are displayed and connections between or among the identified objects indicate their associations. A user may use the information provided in such a graph view and/or one or more related histogram views (see, e.g., FIG. 8C), for example, to determine whether the objects are duplicates or not. In some other embodiments, the connections between or among the identified objects may be shown in an explorer view, wherein a user may click on an icon that represents an object to find out more details about why certain objects are connected to each other and what makes the objects possible duplicates of one another. The created association may indicate the identical matched properties, or possibly only the properties that are deemed crucial.

At decision block 720, the data quality monitor receives input from the user indicating whether or not a set of potential duplicates really are duplicates. For example, the user may review additional properties of identified possible duplicate objects in order to make the determination. The user may provide the input in various manners, such as the user dragging and dropping duplicate objects onto one another, responding to a query from the system requesting confirmation of duplication in illustrated objects, and/or by any other manner. In some embodiments, the data quality monitor may be configured to automatically make a choice by default in case a user is not available or decides not to perform the confirmation step. In such instances, the data quality monitor may automatically make a determination and resolve and/or remove any duplication.

If the user finds that the identified objects are duplicates, the process 600 proceeds to block 625, where the duplication issue is resolved. As discussed above, in one embodiment duplicate objects may be resolved by combining the objects into a single object, having properties from each of the two or more determined duplicate objects. In other embodiments, the duplicate objects may remain separate objects, but associations between or among the identified objects may be updated to indicate the user's confirmation of the duplication. For example, the association among the identified objects may be updated to "confirmed duplicates" from "potential duplicates."

If, however, the user decides that the identified objects may not be duplicates at decision block 620, the process 600 proceeds to block 630, where the indication of possible duplication may be removed by the system. In some embodiments, association between or among the identified objects may also be removed or updated to indicate the use's confirmation of no duplication. For example, the association among the identified objects may be updated to "no duplication-confirmed" from "potential duplicates."

Figure 7:
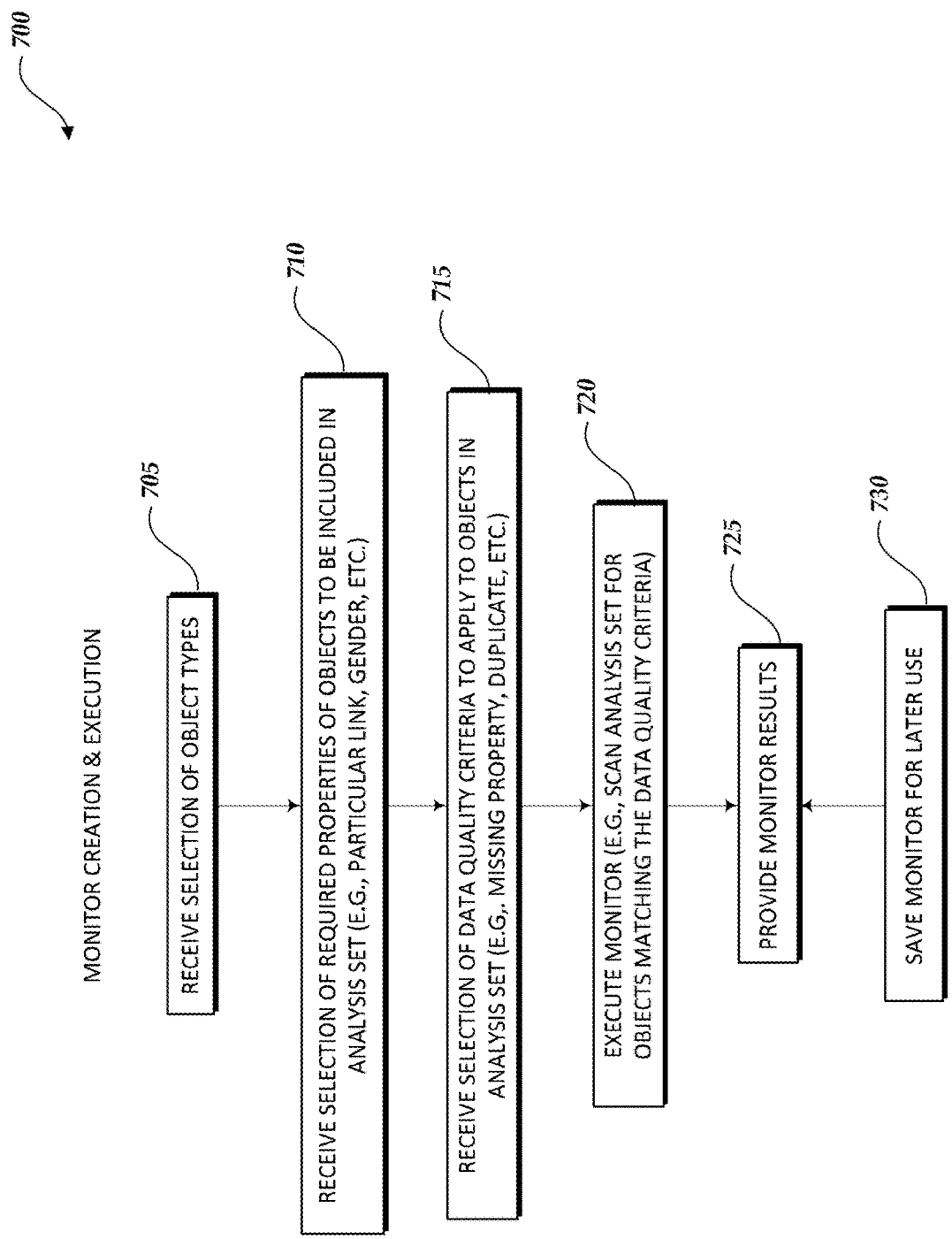
FIG. 7 is a flowchart depicting an illustrative process of creating and running data quality monitors based on received data quality criteria.

FIG. 7 is a flowchart depicting an illustrative process of creating and running data quality monitors based on received data quality criteria, according to one embodiment. The method of FIG. 7 may be performed by a computing system used by an analyst (or other user), one or more server systems that store the object ontology (e.g., database system 210 of FIG. 1), and/or any other suitable computing system.

The process 700 begins at block 705, where the data quality monitor receives selection of object types. In some embodiments, available object types may be presented directly to a user, such as in a drop-down menu. In some other embodiments, the user can choose more than one available object types. For example, as previously discussed, a person object type may be selected.

The process 700 proceeds to block 710, where the data quality monitor receives a selection of required properties of objects to be included in an analysis set. For example, if the selected object type in block 705 is a person object, the selection of required properties for the person objects to be included in the analysis set may include any property of person objects, such as the following, without limitation: name, address, phone number, date of birth, Social Security Number, driver's license, country of citizenship, immigration status, occupation, etc. In some cases, the selection of required properties of objects may include a smaller number of properties that are the most crucial to a user. For example, if a user wants to run a data quality monitor on case objects related to stolen vehicles, the properties associated with the case objects may include Vehicle Identification Number (VIN), date on which the vehicle was stolen, location where the vehicle was last seen, vehicle model, vehicle make, and vehicle color, etc. In some other cases, the selection of required properties may include a large number of properties, depending on the user's requirement. In addition, the object type selected for monitoring may be required to be associated with one or more other object types, such as the required link between person object types and case object types in the example of FIG. 5A.

At block 715, the data quality monitor may receive a selection of data quality criteria to apply to objects in the analysis set. Depending on the embodiment, available data quality criteria may first be determined based on a selected data quality monitor type, such as (1) duplicate objects; (2) multi-valued properties; (3) missing properties; (4) unparsed properties; (5) properties with values that do not match allowed enumerations; (6) numeric range violation, etc. Each data quality monitor type may include certain criteria for identifying objects with potential data quality problems. Additionally, the user can customize the data quality criteria that are included in the monitor. Discussed below are examples of certain data quality monitors that may be selected by a user.

A duplicate objects monitor may identify potentially duplicate objects that have one or more identical (or substantially similar) property values such that they may be considered duplicates. However, objects may not always be considered potentially duplicate just because they share some of the same property values. For example, several person objects may share the same mailing address, phone number, and vehicle information. In some situations, having such identical property values does not make the person objects identical because these people may live in the same household. In some other cases, sharing important property values may result in the system finding that some objects are potentially duplicates. For example, if several person objects share the same Social Security Number, phone number, date of birth, then they might be considered duplicates. In some embodiments, these person objects may still be considered not potentially duplicates due to other property values that are available or fraud concerns. Thus, depending on the particular data objects and corresponding properties that are being monitored, the user may have different criteria for a duplicate objects monitor.

A multi-valued properties monitor may identify objects with properties with more than one value. For example, the President of a foreign country should be only one person. If the value of the President property of that country object has more than one person, this could indicate a potential data quality problem. In another example, a person object has two Social Security Numbers. Normally, a person should only be associated with only one Social Security Number. However, there could be a fraud investigation, and this particular person object has been associated with several Social Security Numbers that he has fraudulently used. Thus, the person object may be flagged as a potential data quality problem in a multi-valued properties monitor.

A missing properties monitor may identify objects with property values missing and/or missing property types. For example, in some embodiments, a blood donor database may include many person objects, each having a property called "blood type." Because it may be important to determine the blood donors' blood types, a person object having no blood type property value or a person object having no blood type property at all may potentially be problematic.

An unparsed properties monitor may identify objects associated with unprocessed and/or incomplete information in an origin database. For example, a field agent in a law enforcement agency may have input the following information regarding a suspect (e.g., a person data object): "loc: CA." Afterwards, if no more information is provided by the field agent, it may not be very clear whether this information means "location=California," "location=Canada" or something else. In another example, a suspect may have provided a date of birth. However, the suspect's date of birth may use a different calendar year system, such as the lunar-year calendar system or the Tibetan calendar system. Therefore, if the suspect's lunar birth date is Jan. 20, 1986, the suspect's real birth date may be a different date. Property values as such may also result in data quality issues.

In another example, a date may be provided in a format such as Day/Month/Year (e.g., 13/7/92). A system that mistook the "Day" for "Month" may fail to parse the date of 13/7/92 because there is no month 13. The unparsed properties monitor may catch dates that fail to parse under the Month/Day/Year convention and alert a user to correct the date parsing rule so that a date provided under the Day/Month/Year format will be parsed correctly.

Depending on the embodiment, an enumerated property may be a property with a restricted or limited set of allowed values. Properties with values that do not match allowed enumerations may result from wrong values that do not correspond to the property types. For example, a person object may have an "age" property with a value of "female" and a "gender" property with a value of "55 years old." In another example, "fmale" may be provided instead of "female" for gender, which may result in data parsing failures. In some situations, a user may mistakenly understand the acceptable values of a property. For example, a user may believe that the location property may have two values such as "CONUS" (meaning Continental U.S.) and "OCONUS (outside Continental U.S.) when in fact the location property has values such as "bar," "park," or "home." The data quality monitor may detect such discrepancies and alert a use to correct the problems accordingly. In some other situations, the problem could be less obvious. For example, a case object may have a "stolen vehicle" property with a value of "Escape at Lincoln St." The field agent who originally entered the information may have meant that the vehicle was stolen while it was on Lincoln St., and the stolen vehicle is a Ford Escape. However, since the information has not been parsed properly, it may present an unparsed properties issue. Depending on embodiments and user requirements, such discrepancies in property values may be detected by a data quality monitor using parameters specified by the user and/or parameters set up by the system.

A numeric range violation monitor may identify objects with property values outside of an expected range for the particular property. For example, a person object may have an "age" property with a value of "−10" or "450." Both are clearly wrong. More subtle mistakes can also be detected. For example, if the system has knowledge that a certain street's street numbers are 0 to 100, then the system may be able to find an erroneous street address value with a street number of 150. In some other embodiments, a data range violation monitor may also be provided. For example, if a provided date is invalid or is out of context (e.g., a credit card transaction date in the $14^{th}$ Century), the data quality monitor may catch such problems and alert the user.

Once a data quality monitor type is selected and criteria of the monitor are established, the process 700 proceeds to block 720, where the data quality monitor is executed. For example, the data quality monitor may scan the analysis set for objects matching the specified data quality criteria and/or a set of system default criteria.

At block 725, results of the execution of data quality monitor are provided. In some embodiments, such results are provided in a graphical user interface, listing all the objects and/or their specific values that may have violated the defined data quality criteria. In some other embodiments, such results may be provided in a graphical user interface that connects the objects in order to allow the users to see how such objects are connected. For example, as previously discussed, two potentially duplicate objects may be connected by an association named "possibly same as," showing that the two objects are deemed to be possible duplicates. Depending on the embodiment, the graphical user interface may also include property values showing why the identified objects are included. In some other embodiments, the results may also be stored in a file such as a comma-delimited file, an Excel® file, an XML file, an HTML file, etc., with information such as name of the objects and/or property values. In some embodiments, the results may be available for users to download.

At block 730, a user may be given the choice of saving the data quality monitor for later use. If the user chooses to do so, in some embodiments, the results of several rounds of data quality monitoring may also be compared to see whether the same data quality issues tend to persist, and whether some data quality problems have already been resolved. In some other embodiments, a user may not only save data quality monitors, but also publish them so that other users of the system may also run similar or the same searches to detect data quality issues. Depending on the embodiment, other users may use a published data quality monitor and customize the monitor for their own specific requirements.

FIG. 8A illustrates an example user interface 840 that allows a user to create, load, and/or update criteria for a data quality monitor according to one embodiment. The example user interface 840 includes choices of creating a new monitor 853 or selecting an existing data quality monitor 850. In some embodiments, if a user chooses to create a new data quality monitor 853, the user interface 840 may present choices/questions to the user so that the user may specify criteria to be included in the new data quality monitor. If a user chooses to select an existing data quality monitor 850, criteria of the selected data quality monitor are loaded into the system for execution. The example user interface 840 allows the user to further customize an existing data quality monitor and save the customized data quality monitor as a new monitor. In some other embodiments, a data quality monitor may be configured such that it can only be customized or edited by certain users.

The user interface 840 includes options that allow a user to configure the objects to monitor 855. In this example, the objects selected to be monitored are case objects. Other types of objects can also be monitored. Moreover, in some embodiments, a user may edit objects so that more than one type of objects may be monitored. In some embodiments, even if monitoring is only performed on one type of object, data quality monitoring criteria may require the monitored object to be associated with one or more other types of objects. For example, a case object may be required to be associated with at one or more event objects and/or person objects that are of interest to a user.

The example user interface 840 further includes a monitor type selection control 860 that allows selection of a data quality monitor type. As previously discussed, available data quality monitor types may include: (1) potentially duplicate objects; (2) multi-valued properties; (3) missing properties; (4) unparsed properties; (5) properties with values that do not match allowed enumerations; (6) numeric range violation, and/or any other monitor. In the example of FIG. 8A, potentially duplicate objects 860 is selected. Once a data quality monitor type is selected, specific properties of the selected objects to be monitored may be provided by the user. Customization of properties is discussed further with reference to the example of FIG. 8B.

In some embodiments, data quality monitor settings may also be configured to discover orphaned objects, such as objects with no links. Data quality monitor settings may also be limited to run the search criteria specified, e.g., in 855, exclusively without checking for anything else.

FIG. 8B illustrates another example user interface 1100 wherein a user has configured a potentially duplicate person monitor to identify person objects (linked to case objects) that are potentially duplicates. Thus, as displayed in the area 1125, person objects linked to case objects are configured to be monitored. The required association of person objects to case objects may be a user's desire to monitor only person objects that have some connection to a criminal investigation (e.g., "case").

In the drop-down menu 1130 in this example, the selected data quality criterion is potentially duplicate objects (potentially duplicate person) and the minimum number of properties satisfying the property requirements is selected as two at box 1135.

In this example, the user has selected properties to match on as: name 1140, date of birth 1145, Social Security Number 1150, and license number 1155. Therefore, according to the settings in user interface 1100, the objects found to be potentially duplicates should have at least two identical property values, which can be any two properties from the four selected properties. Thus, for this particular monitor, two objects sharing the same name and Social Security Number would be considered possible duplicates and may be presented to the user for further confirmation and/or resolution.

As discussed previously, objects matching the criteria specified in a data quality monitor may be displayed in the user interface 1100. In this example, a total of three groups of objects are found, as indicated in 1160. The eleven identified person objects are all related to a case object(s) per the link requirement indicated in area 1125. In this example, the eleven located person objects are displayed in interface 1165, along with connections between the identified person objects.

FIG. 8C illustrates an example user interface 870 wherein a group of possibly duplicate person objects are displayed and properties of these person objects are shown to indicate properties of the objects, which may be useful to the user in determining whether the objects really are duplicates. In this example, a group of five person objects (e.g., of the three groups of objects located in the example of FIG. 8B) are displayed and an entity properties histogram 871 is illustrated to show various properties of the identified objects. As shown at 874, the five person objects have the name "James Bond" or names very similar to "James Bond," such as "James B." Furthermore, some of the identified person objects share other properties. In this example, all five person objects have the same social security number, as shown in 878. Four of the five objects have the same date of birth (at 872) and three of the person objects share the same last name "Bond" (at 876). Finally, all five identified person objects in this example have at least three properties (as required by a user by specifying minimum matches=3) that match another person object. Given the information provided about the identified properties, the user may be able to confirm whether any or all of the identified objects should be considered duplicates or not. If a user confirms that some of the identified objects are in fact duplicates, he or she may take further actions such as resolving the duplication and/or updating the associations among person objects.

Figure 9:
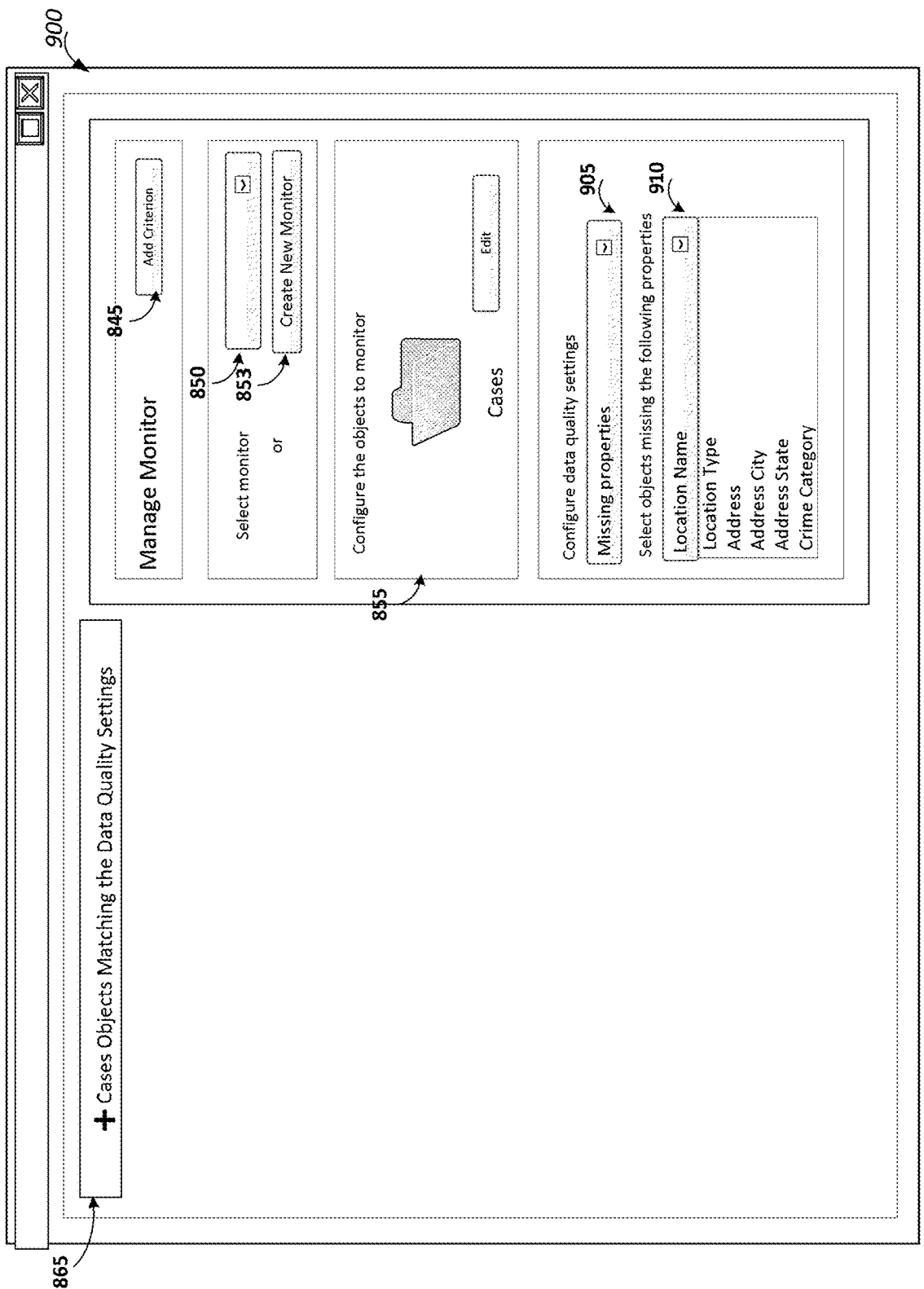
FIG. 9 illustrates an example user interface wherein a user has selected a missing properties monitor and is provided with example object properties to select for monitoring.

FIG. 9 illustrates an example user interface 900 wherein a user has selected a missing properties monitor and is provided with object properties to select for monitoring. In this example, the objects being monitored are case objects. As previously discussed, missing properties may include data quality issues resulting from absent property values associated with one or more properties and/or missing property types altogether. In this example, the user interface 900 includes a list of properties associated with the case object so that a user may choose which properties and/or property values to monitor.

In this example, the list of properties for user selection in the drop-down menu 910 includes: (1) location name; (2) location type; (3) address; (4) address city; (5) address state; (6) crime category. In this example, the user has chosen to monitor "location name" in order to identify case objects missing either the property "location name" or objects with no value associated with the "location name" property. The user interface 900 also allows the user to choose to monitor more case properties for missing properties, such as by selecting the add criterion button 845. In some embodiments, other properties associated with a case object may be presented for user selection. In some other embodiments, instead of presenting the properties that a user may choose to monitor in a drop-down menu, other types of user interface elements may be used.

Figure 10:
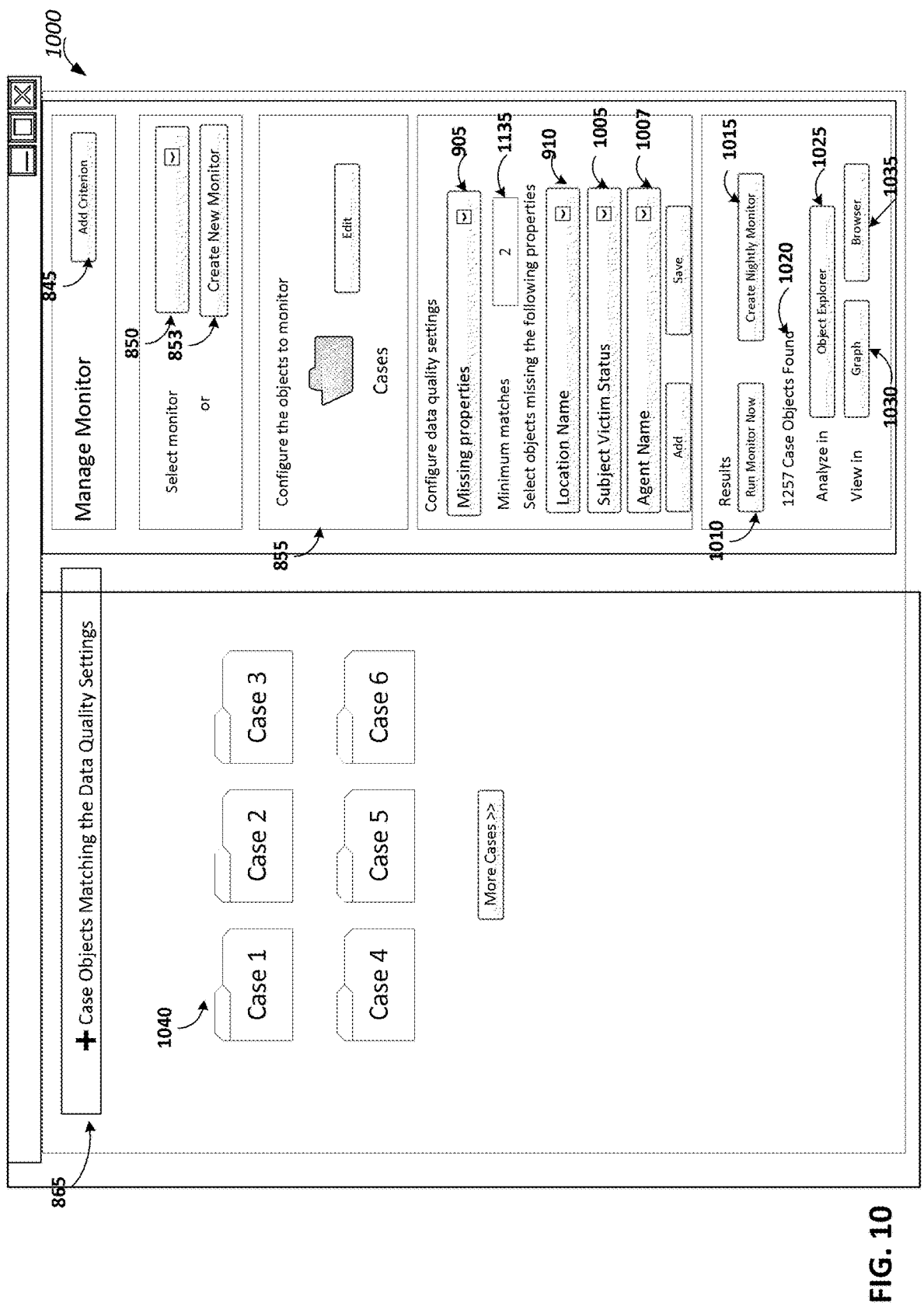
FIG. 10 illustrates an example user interface that displays multiple case objects that were identified in an executed missing properties monitor.

FIG. 10 illustrates an example user interface 1000 that displays multiple case objects that were identified in an executed missing properties monitor. In this example, multiple properties associated with an object have been selected for inclusion in the missing properties monitor. In particular, in addition to a "location name" property in 910, "subject victim status" is selected in 1005 and Agent Name is selected in 1007.

Depending on the embodiment, the user interface 1000 may also include one or more Boolean logic operator between or among the properties selected by a user. For example, a user may be able to specify that she wants to monitor case objects missing both the "location name" property (or property value) and the "subject victim status" property (or property value). In another example, a user may specify that she only wants to monitor case objects missing either the "location name" property (or property value) or the "subject victim status" property (or property value). The user interface 1000 allows the users to specify a minimum number of matches in box 1135 or some other user interface elements. In this example, a minimum of two matches is required and, thus, objects located by this monitor match at least two of the three specified properties.

In a similar manner as discussed above with reference to FIGS. 8-9, for example, data quality monitors of other types, such as unparsed properties, may present a list of available properties for users to choose from in customizing the monitors. In an unparsed properties example, one or more Boolean logic operators may be provided to specify whether all the properties selected by the user are required to have unparsed properties or only one or a subset of the properties are required to have unparsed properties.

The user interface 1000 may also include options for users to run monitor now 1010 or create nightly monitor 1015. If a user chooses to create nightly monitors, the user interface 1000 may in some embodiments ask further questions such as the specific time that the configured data quality monitor should be executed and how the user wish to review the data quality monitor results. If a user chooses to run the configured data quality monitor now, the user interface 1000 may send commands to execute the data quality monitor. After execution, the user interface 1000 may display a quantity of objects matching the data quality monitor and/or display the matched objects.

In the example of FIG. 10, 1257 case objects were found as shown at 1020. The user interface may present a choice to analyze the matched objects using an Object Explorer by choosing 1025. In some embodiments, the user interface 1000 may also include choices for users to view the matched objects in a graph by choosing 1030 or in a browser by choosing 1035.

Depending on the embodiment, the user interface 1000 may also display the objects matching the configured data quality settings in the executed data quality monitor. In this example, the user interface includes an area 865 displaying case objects matching the data quality settings. The first six case objects 1040 are displayed as case 1 through 6. A different default number of objects may be displayed by the user interface 1000 as needed or according to a different user setting.

Implementation Mechanisms

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 11:
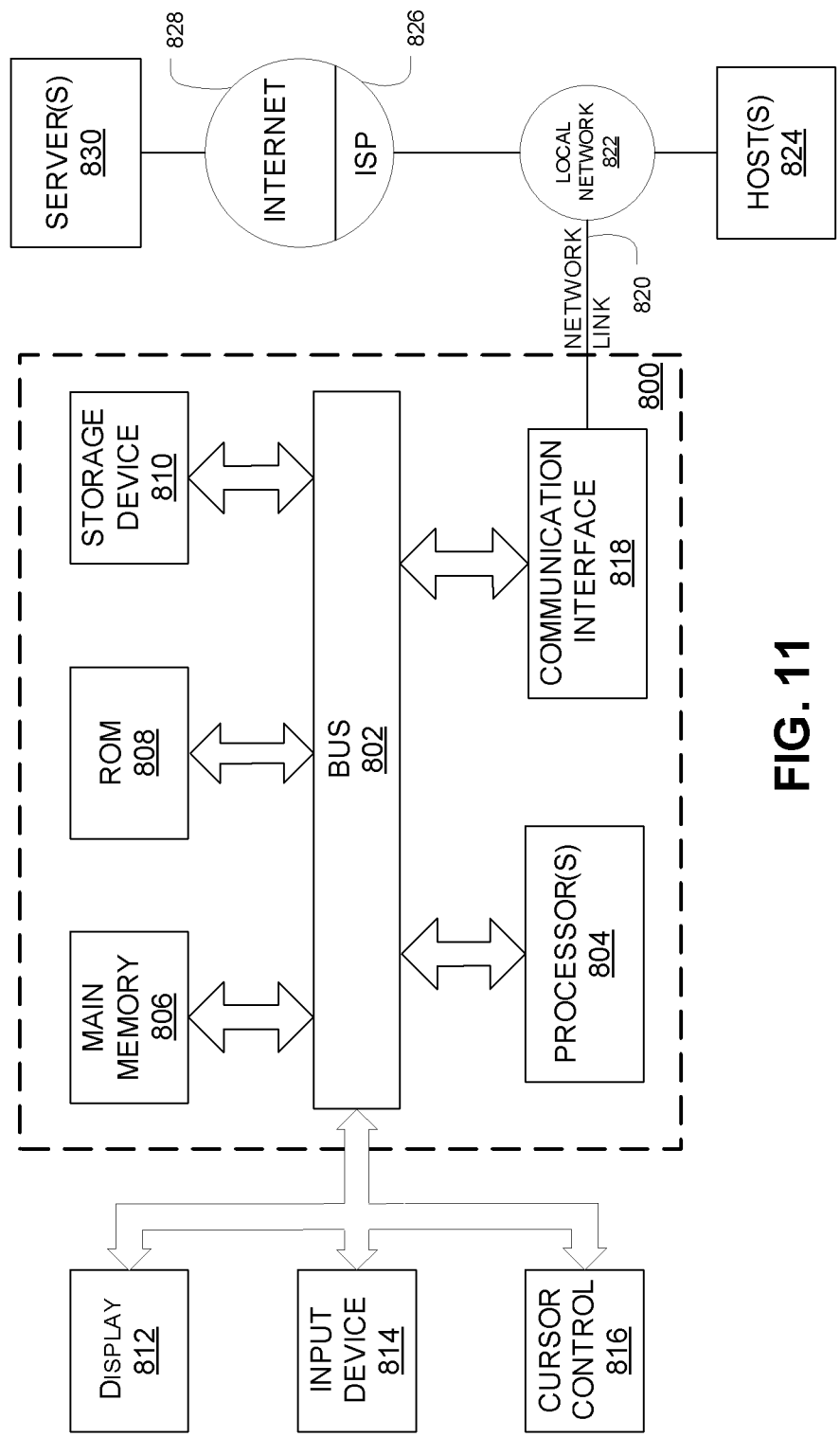
FIG. 11 illustrates a computer system with which certain methods and modules discussed herein may be implemented.

For example, FIG. 11 is a block diagram that illustrates a computer system 800 upon which an embodiment may be implemented. Computer system 800 includes a bus 802 or other communication mechanism for communicating information, and a hardware processor, or multiple processors, 804 coupled with bus 802 for processing information. Hardware processor(s) 804 may be, for example, one or more general purpose microprocessors.

Computer system 800 also includes a main memory 806, such as a random access memory (RAM), cache and/or other dynamic storage devices, coupled to bus 802 for storing information and instructions to be executed by processor 804. Main memory 806 also may be used for storing temporary variables or other intermediate information during execution of instructions to be executed by processor 804. Such instructions, when stored in storage media accessible to processor 804, render computer system 800 into a special-purpose machine that is customized to perform the operations specified in the instructions.

Computer system 800 further includes a read only memory (ROM) 808 or other static storage device coupled to bus 802 for storing static information and instructions for processor 804. A storage device 810, such as a magnetic disk, optical disk, or USB thumb drive (Flash drive), etc., is provided and coupled to bus 802 for storing information and instructions.

Computer system 800 may be coupled via bus 802 to a display 812, such as a cathode ray tube (CRT) or LCD display (or touch screen), for displaying information to a computer user. An input device 814, including alphanumeric and other keys, is coupled to bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 800 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage Computer system 800 may implement the techniques described herein using customized hard-wired logic, one or more ASICs or FPGAs, firmware and/or program logic which in combination with the computer system causes or programs computer system 800 to be a special-purpose machine. According to one embodiment, the techniques herein are performed by computer system 800 in response to processor(s) 804 executing one or more sequences of one or more instructions contained in main memory 806. Such instructions may be read into main memory 806 from another storage medium, such as storage device 810. Execution of the sequences of instructions contained in main memory 806 causes processor(s) 804 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 810. Volatile media includes dynamic memory, such as main memory 806. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise bus 802. Transmission media can also take the form of acoustic or light waves, such as those generated during radio-wave and infra-red data communications.

Various forms of media may be involved in carrying one or more sequences of one or more instructions to processor 804 for execution. For example, the instructions may initially be carried on a magnetic disk or solid state drive of a remote computer. The remote computer can load the instructions into its dynamic memory and send the instructions over a telephone line using a modem. A modem local to computer system 800 can receive the data on the telephone line and use an infra-red transmitter to convert the data to an infra-red signal. An infra-red detector can receive the data carried in the infra-red signal and appropriate circuitry can place the data on bus 802. Bus 802 carries the data to main memory 806, from which processor 804 retrieves and executes the instructions. The instructions received by main memory 806 may retrieves and executes the instructions. The instructions received by main memory 806 may optionally be stored on storage device 810 either before or after execution by processor 804.

Computer system 800 also includes a communication interface 818 coupled to bus 802. Communication interface 818 provides a two-way data communication coupling to a network link 820 that is connected to a local network 822. For example, communication interface 818 may be an integrated services digital network (ISDN) card, cable modem, satellite modem, or a modem to provide a data communication connection to a corresponding type of telephone line. As another example, communication interface 818 may be a local area network (LAN) card to provide a data communication connection to a compatible LAN (or WAN component to communicated with a WAN). Wireless links may also be implemented. In any such implementation, communication interface 818 sends and receives electrical, electromagnetic or optical signals that carry digital data streams representing various types of information.

Network link 820 typically provides data communication through one or more networks to other data devices. For example, network link 820 may provide a connection through local network 822 to a host computer 824 or to data equipment operated by an Internet Service Provider (ISP) 826. ISP 826 in turn provides data communication services through the world wide packet data communication network now commonly referred to as the "Internet" 828. Local network 822 and Internet 828 both use electrical, electromagnetic or optical signals that carry digital data streams. The signals through the various networks and the signals on network link 820 and through communication interface 818, which carry the digital data to and from computer system 800, are example forms of transmission media.

Computer system 800 can send messages and receive data, including program code, through the network(s), network link 820 and communication interface 818. In the Internet example, a server 830 might transmit a requested code for an application program through Internet 828, ISP 826, local network 822 and communication interface 818.

The received code may be executed by processor 804 as it is received, and/or stored in storage device 810, or other non-volatile storage for later execution.

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computer-implemented method, performed by a computing system having one or more hardware computer processors and one or more non-transitory computer readable storage device storing software instructions executable by the computing system to perform the computerized method comprising:
   receiving, via a user interface, selection, from a plurality of object types including entity and event, a first object type and a related object type different than the first object type;
   receiving, via the user interface, selection of a criterion selected from a plurality of criterion that are selectable via the user interface, wherein the selected criterion is configured to identify data objects of the first object type associated with a data object of the related object type and having a potential problem;
   identifying, based on evaluation of at least the selected criterion with reference to a plurality of data objects stored in one or more data stores:
      a first data object of the first object type, the first data object having a plurality of properties, wherein the first data object is identified based on satisfaction of the selected criterion by one or more properties of the first data object; and
      a second data object of the related object type having a link to the first data object; and
   causing presentation, in the user interface, of a graphical representation of the first and second data objects as visually linked.

2. The computer-implemented method of claim 1, wherein the potential problem comprises at least one of: possible duplicate objects, missing properties, multi-valued properties, unparsed properties, disallowed enumerations, numeric range violations, or date range violations.

3. The computer-implemented method of claim 1, wherein the criterion comprises a value for a property.

4. A non-transitory computer storage medium storing computer executable instructions that when executed by a computer hardware processor perform operations comprising:
- receiving, via a user interface, selection, from a plurality of object types including entity and event, a first object type and a related object type different than the first object type;
- receiving, via the user interface, selection of a criterion selected from a plurality of criterion that are selectable via the user interface, wherein the selected criterion is configured to identify data objects of the first object type associated with a data object of the related object type and having a potential problem;
- identifying, based on evaluation of at least the selected criterion with reference to a plurality of data objects stored in one or more data stores:
  - a first data object of the first object type, the first data object having a plurality of properties, wherein the first data object is identified based on satisfaction of the selected criterion by one or more properties of the first data object; and
  - a second data object of the related object type having a link to the first data object; and
- causing presentation, in the user interface, of a graphical representation of the first and second data objects as visually linked.

5. The non-transitory computer storage medium of claim 4, wherein determining the second data object further comprises identifying a first property of the first data object that matches a second property of the second data object.

6. The non-transitory computer storage medium of claim 5, wherein the potential problem comprises a possible duplicate object, and the operations further comprise:
- receiving a user selection to resolve the potential problem;
- generating a merged data object including a property from at least one of the first or second data objects;
- removing at least one of the first or second data objects from a data store; and
- storing the merged data object in the data store.

7. The non-transitory computer storage medium of claim 4, wherein the operations further comprise:
- generating a data quality monitor including the first object type and the criterion; and
- storing the data quality monitor in a data store, wherein the data quality monitor is executable to identify potential data problems.

8. A computer system comprising:
- one or more hardware computer processors programmed, via executable code instructions, to:
  - receiving, via a user interface, selection, from a plurality of object types including entity and event, a first object type and related object type different than the first object type;
  - receiving, via the user interface, selection of a criterion selected from a plurality of criterion that are selectable via the user interface, wherein the selected criterion is configured to identify data objects of the first object type associated with a data object of the related object type and having a potential problem;
  - identifying, based on evaluation of at least the selected criterion with reference to a plurality of data objects stored in one or more data stores;
    - a first data object of the first object type, the first data object having a plurality of properties, wherein the first data object is identified based on satisfaction of the selected criterion by one or more properties of the first data object; and
    - a second data object of the related object type having a link to the first data object; and
  - causing presentation, in the user interface, of a graphical, representation of the first and second data objects as visually linked.

9. The computer system of claim 8, wherein identifying the first data object of the first object type with the potential problem further comprises matching the criterion with a property of the first data object.

10. The computer system of claim 8, wherein determining the second data object further comprises identifying a first property of the first data object that matches a second property of the second data object.

11. The computer system of claim 8, wherein the potential problem comprises a possible duplicate object, and the one or more hardware computer processors are further programmed to:
- receive a user selection to resolve the potential problem; and
- generate a merged data object including a property from at least one of the first or second data objects.

12. The computer system of claim 11, wherein the one or more hardware computer processors are further programmed to:
- remove at least one of the first or second data objects from a data store.

13. The computer system of claim 11, wherein the one or more hardware computer processors are further programmed to:
- store the merged data object in a data store.

14. The computer system of claim 10, wherein the one or more hardware computer processors are further programmed to:
- generate a data quality monitor including the first object type and the criterion; and
- store the data quality monitor in a data store, wherein the data quality monitor is executable to identify potential problems.

* * * * *

UNITED STATES PATENT AND TRADEMARK OFFICE
CERTIFICATE OF CORRECTION

| | | |
|---|---|---|
| PATENT NO. | : 10,970,261 B2 | Page 1 of 1 |
| APPLICATION NO. | : 15/158410 | |
| DATED | : April 6, 2021 | |
| INVENTOR(S) | : Malina Kirn | |

It is certified that error appears in the above-identified patent and that said Letters Patent is hereby corrected as shown below:

On the Title Page

On Page 4, Column 1, Item (56), Line 24, under Other Publications, delete "7Qs0D0Kc." and insert -- 7Qis0D0kc. --.

In the Specification

In Column 10, Line 48, delete ""category =8D"" and insert -- "category=8D" --.

In Column 10, Line 49, delete ""category =8F"" and insert -- "category=8F" --.

In Column 10, Line 52, delete "location =Boston," and insert -- location=Boston, --.

In Column 10, Line 53, delete "airLine =Southwest," and insert -- airLine=Southwest, --.

In Column 15, Line 59, delete "20," and insert -- 20$^{th}$, --.

In the Claims

In Column 25, Line 53, Claim 8, delete "and related" and insert -- and a related --.

In Column 26, Line 9, Claim 8, delete "stores;" and insert -- stores: --.

In Column 26, Lines 17-18, Claim 8, delete "graphical, representation" and insert -- graphical representation --.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*